US008940541B2

(12) United States Patent
Graf et al.

(10) Patent No.: US 8,940,541 B2
(45) Date of Patent: Jan. 27, 2015

(54) DEVICE, SYSTEM AND METHOD FOR STORING AND SORTING CELLULAR SAMPLES

(75) Inventors: Siegfried Graf, Luzern (CH); Helmut Knapp, Ebikon (CH); Noa Schmid, Kriens (CH)

(73) Assignee: CSEM—Centre Suisse d'Electronique et de Microtechnique SA—Recherche et Developpement, Neuchâtel (CH)

( * ) Notice: Subject to any disclaimer, the term of this patent is extended or adjusted under 35 U.S.C. 154(b) by 912 days.

(21) Appl. No.: 12/554,078

(22) Filed: Sep. 4, 2009

(65) Prior Publication Data

US 2010/0062480 A1 Mar. 11, 2010

Related U.S. Application Data

(60) Provisional application No. 61/094,658, filed on Sep. 5, 2008.

(51) Int. Cl.
| | |
|---|---|
| *C12Q 1/02* | (2006.01) |
| *C12Q 1/00* | (2006.01) |
| *C12M 1/00* | (2006.01) |
| *G01N 35/08* | (2006.01) |
| *G01N 15/14* | (2006.01) |

(52) U.S. Cl.
CPC ............. *G01N 15/14* (2013.01); *G01N 35/08* (2013.01); *G01N 2015/149* (2013.01)
USPC .......................................................... 436/94

(58) Field of Classification Search
CPC .............. C12Q 1/02; C12Q 1/00; C12M 1/00
USPC ............................................................ 422/73
See application file for complete search history.

(56) References Cited

U.S. PATENT DOCUMENTS

| | | | | | |
|---|---|---|---|---|---|
| 2,614,110 | A | * | 10/1952 | Davis ............................. | 554/18 |
| 3,161,581 | A | * | 12/1964 | Tiedje et al. ................. | 208/390 |
| 3,572,500 | A | * | 3/1971 | Kouloheris ...................... | 209/5 |
| 5,578,269 | A | * | 11/1996 | Yaremko et al. ............... | 422/64 |
| 5,924,972 | A | * | 7/1999 | Turvaville et al. ............. | 494/11 |
| 6,074,613 | A | * | 6/2000 | Harness et al. .............. | 422/534 |
| 6,328,897 | B1 | * | 12/2001 | Leung ........................... | 210/744 |
| 6,371,717 | B1 | * | 4/2002 | Grams et al. ............ | 414/416.09 |
| 2002/0033939 | A1 | | 3/2002 | Hansen | |
| 2005/0214947 | A1 | * | 9/2005 | Cox ................................ | 436/45 |

OTHER PUBLICATIONS

Nakayama, et al. "Introduction to Fluid Mechanics; Chaper 9." Publication Year 2000. 26 pages.*

(Continued)

*Primary Examiner* — Christine T Mui
(74) *Attorney, Agent, or Firm* — A.C. Entis-IP Ltd.

(57) ABSTRACT

The present invention discloses a sample sorter system adapted to receive and sort samples according to predetermined criteria. The sample sorter system comprises a receptacle that is adapted to receive and retain fluid and samples. The receptacle is operatively coupled with a drive and with a power source such that actuation of the drive causes the rotation of at least one circular component, which in turn causes the development of a flow regime in the receptacle such that the samples suspended in the fluid are conveyable along a closed path to at least one sample handling site that are positioned along said closed path.

20 Claims, 11 Drawing Sheets

(56) References Cited

OTHER PUBLICATIONS http://www.unionbio.com/products/copas2.html, website visited Aug. 13, 2009.

COPAS sorting platform; COPAS Instruments for large particle flow cytometry; (http://www.unionbio.com/products/copas2.html) website visited Aug. 13, 2009.

* cited by examiner

DEVICE, SYSTEM AND METHOD FOR STORING AND SORTING CELLULAR SAMPLES

CROSS-REFERENCE TO RELATED APPLICATIONS

This patent application claims priority from U.S. Provisional Patent Application No. 61/094,658 filed on Sep. 5, 2008, the disclosure of which is incorporated herein by reference in its entirety.

FIELD OF THE INVENTION

Generally, the present invention refers to the field of the handling of sortable samples including, for example, *Xenopus oocytes*, Zebrafish larvae or embryos, beads, pollen, cells and cell-clusters. In particular, the present invention refers to the storage, sorting, and dosing of samples.

BACKGROUND OF THE INVENTION

Cellular samples are for some applications the preferred choice of screening in drug discovery research, potentially overtaking more traditional approaches that include animal models. The cellular samples may be used to detect specific cellular pathways of chemical compounds, therapeutic proteins, synthetic ribonucleic acid (siRNA) agents and other structures of interest. Insights from these samples could enable more efficient discovery of effective drugs compared to non-cell-based samples, thus saving time and costs as well as the need for future secondary screens. However, cellular samples usually vary from one another in terms of their usability for screening. For example, in order to perform screening on cellular samples they must exhibit certain viability. Several parameters provide an indication of a selected sample's viability such as size, form, color, and the presence of certain types of molecules. To avoid the waste of valuable resources needed for the screening of cell samples like man hours, equipment, chemical substances and compounds, the separation or sorting of usable cellular samples from non-usable ones is thus desired prior to performing any screening process. The sorting of cellular samples is done by cell sorters known in the art, which are usually adapted to receive a mixture of, e.g., cellular samples and which partition the mixture into separate cell samples according to cell types for further individual processing. Such a separated cellular sample may be a single cell or a group of cells of the same type. In particular, cellular samples may refer to any of the following: *Xenopus oocytes*, zebrafish larvae or embryos, pollen, cells, cell-clusters, or to any other cellular matter.

Cell sorters, which are also referred to as flow cytometers, are guiding the mixture into a nozzle which generates a jet of liquid having suspended therein the cellular samples such that individual cellular samples of the mixture are ejected from the nozzle outlet. The nozzle outlet is positioned in relation to a laser source in a manner such that ejected cellular samples may pass laser light emitted by the laser source. At least some of the ejected cellular samples interact with the ejected cellular samples causing scattering of the laser light and fluorescing of at least some of the ejected cellular samples. The photons of the fluorescing light and the scattered laser light are collected by photomultipliers. The multiplied photons pertaining to fluorescening light and scattered laser light are subsequently analyzed cytometrically to determine according to predetermined criteria if there are cellular samples for which additional examination is desirable and which are sorted accordingly. To enable the sorting of the individual cell samples, the jet of fluid at the nozzle outlet is formed into droplets containing the individual cell samples, wherein the droplets are electrically charged. The droplets, and thus the individual cell samples, become sortable towards separate collection vials by applying a static electric field according to preselected criteria after the individual cell samples pass the laser light. Alternatively, to sort individual cellular samples, collection vials may be moved into or out of the jet of fluid, or puffs of air can be used to respectively guide individual cellular samples into designated vials according to the preselected criteria. The latter method which employs puffs of air is implemented by the COPAS Sorting Platform. The throughput of such cell sorters can be as high as 100,000 cells per second and numerous measurable parameters are available with the above explained systems.

Patent document US 2002/033939 discloses such a cell sorter for analyzing and dispensing objects larger than about 70 µm in diameter. The cell sorter implements a flow cytometer having a fluidic switch arrangement for diverting a portion of a sample stream in response to detector signals. The cell sorter is particularly adapted for dispensing multicellular test organisms like nematodes or large microspheres for use in screening large libraries of potential pharmaceutical agents. Hydrodynamic focusing is used to center and align the objects in the flow cell. The objects pass through a sensing zone where optical or other characteristics of the objects are detected. The detector signals are processed and used to operate a fluidic switch that is located downstream from the sensing zone. The fluid stream containing the detected objects emerges from the flow cell into air where a fluid stream controlled by the fluidic switch diverts portions of the stream containing no sample objects or sample objects not meeting predetermined at least one criterion. The non-diverted sample stream deposits selected sample objects into a plurality of containers. To ensure reliable analysis of the samples, the throughput of the above outlined systems may have to be reduced down to approximately 10'000 individual cells per seconds. However, fluorescence markers may cause damages to the samples and under certain circumstances the number of parameters that can be determined when employing fluorescence-based procedures is limited. For example, the parameters that may be determined for opaque cells may be limited to the cell's diameter and optical density, since only forward and side scattered laser light may be measurable.

The above-outlined cell sorter does not have any storage capabilities and does not offer a controllable sample-removal mechanism to a subsequent apparatus for performing further treatment and/or analysis of the sorted cells. In addition, these cell sorters may not be adapted to handle and sort samples having diameters in the millimeter range such that the samples, which may for example refer to *Xenopus laevis oocyte* and Zebrafish embryos, have to be sorted manually, which is an arduous and laborious task.

BRIEF DESCRIPTION OF THE FIGURES

Features of the invention will become more clearly understood in the light of the ensuing description of a some embodiments thereof, given by way of example only, with reference to the accompanying figures, wherein.

DESCRIPTION OF THE EMBODIMENTS OF THE INVENTION

Figure 1:
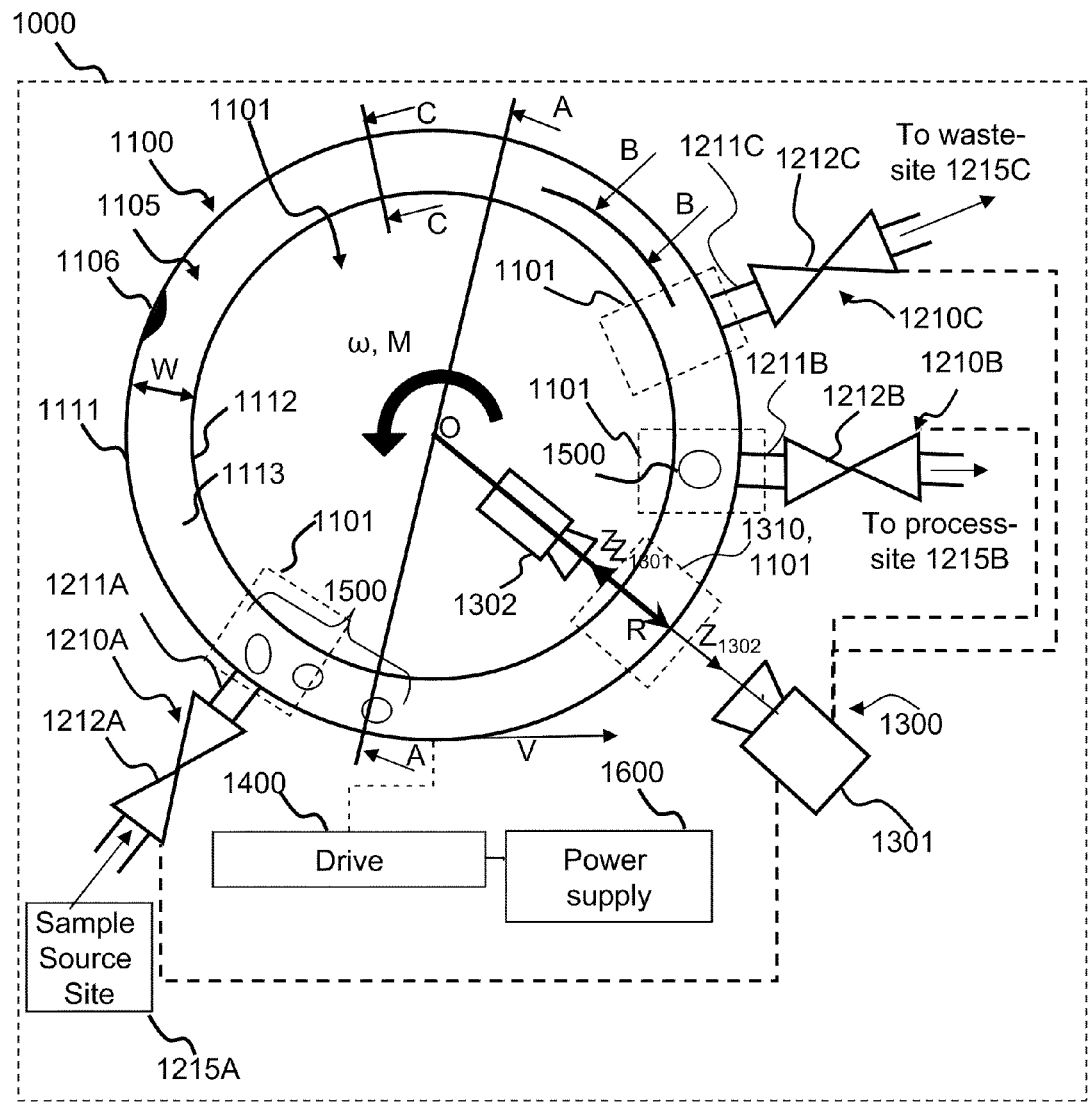
FIG. 1 is a schematic top view illustration of a sample sorter system and device, according to an embodiment of the invention.

Summary of the Embodiments of the Invention

The present invention discloses a sample sorter system adapted to receive and sort samples according to predetermined criteria.

In embodiments, the sample sorter system includes a receptacle that is adapted to receive and fluid and samples. In some embodiments, the fluid may be retained in the receptacle.

In embodiments, the receptacle is operatively coupled with a drive and with a power source such that actuation of the drive causes the rotation of at least one circular component, which in turn causes the development of a flow regime in the receptacle such that the samples suspended in said fluid are conveyable along a closed path to at least one sample handling site that is positioned along the closed path.

In embodiments, the receptacle comprises at least one rotatable component delineating a circular transporting route for the transport of samples therein.

In embodiments, the receptacle is adapted to receive samples and fluid from a sample source site.

In embodiments, the at least one rotatable component is rotatable along the circular transporting route by a drive at a velocity causing samples suspended in the fluid to become subjected to propelling forces such that at least one of said samples is conveyed to at least one of the at least one sample handling site.

In embodiments, the at least one rotatable component is an annular conduit.

In embodiments, the rotatable component is an annular section disassociated from direct frictional contact with the samples such that during rotation of said rotatable component, the samples are subjected to propelling forces corresponding to the generated flow regime only.

In embodiments, the rotatable component is at least one of the following: the annular inner side wall; annular outer side wall; annular cover; and annular ground of the annular conduit.

In embodiments, the at least one sample-handling site includes an examination-site comprising at least one sensor adapted to determine at least one of the following: whether a sample is present, whether a sample passed said examination-site, and the characteristics of parameters of samples passing said examination-site.

In embodiments, the at least one sensor is implemented by at least one of the following group: at least one camera, at least one capacitance-based sensor, at least one light barrier and at least one fluorescence-based sensor.

In embodiments, the sensor includes a plurality of cameras for imaging the entire surface of the samples.

In embodiments, the sample sorter system includes a sample-removal piping that is selectably operatively coupleable with the receptacle such to enable selective removal of the samples during the rotation of the receptacle.

In embodiments, the sample-removal piping employs at least one of the following: a release valve, a suction pump and a sample elutriator.

In embodiments, the receptacle is configured such that said samples are successively alignable in said receptacle.

In embodiments, the receptacle is adapted to convey samples having a diameter ranging from 20-2000 micron.

In embodiments, the at least one sample-handling site operatively communicates with at least one of the following: a supply-piping, a process-piping, a waste-piping and a sample return feed line, wherein said return feed line provides extracted samples back to the annular conduit.

In embodiments, the sample sorter system includes a fluid balancing mechanism ensuring that the volume contained in the annular conduit remains at least approximately constant during the sorting process to prevent overflow or unwanted depletion of fluid from the receptacle.

In embodiments, a method for sorting samples includes the following procedures: providing samples to a receptacle.

In embodiments, the method includes conveying samples in the receptacle to at least one sample-handling site.

In embodiments, the method includes determining characteristics of the samples.

In embodiments, the method includes determining whether the characteristics of the samples meet at least one criterion.

In embodiments, the method includes making a selection of the samples according to the determined characteristics.

In embodiments, the method includes providing the selected samples according to the determined characteristics to either one of the following: a process-site and a waste-site.

Detailed Description of the Embodiments of the Invention

It is an object of the invention to provide a sample sorter device, system and method enabling the reception, sorting and storage and, in some embodiments of the invention, also selective delivery on demand of an individual sample to subsequent apparatuses for further treatment and/or analysis, including samples having a diameter of up to, e.g., 2000 µm.

Accordingly, the sample sorter may in respective embodiments of the invention be operatively coupled with a previous and/or subsequent apparatus, or may be standalone. The term "sample" as used herein may refer to any sortable samples such as, for example, *Xenopus Laevis Oocyte*, zebrafish larvae or embryos, beads, pollen, cells, cell-clusters, a mixture of cells, to a cell aggregate or to any biological and/or organic and/or inorganic entity or matter that can be handled by the sample sorter system, device and method according to embodiments of the current invention.

Moreover, the device, system and method according to embodiments of the invention is adapted to analyze opaque samples in a fluorescence-less manner (i.e., without the need of employing fluorescence-based methods or otherwise stated, in a manner that is free of fluorescence markers or labels) for a variety of parameters such as, for example, the type of sample, sample volume, viability, as well as other physical and/or chemical characteristics.

It should be understood that where the claims or specification refer to "a" or "an" feature, such reference is not to be construed as there being only one of that element. Accordingly, "an" or "a" feature may also encompass the meaning of "at least one" of the feature. For example, "a sample" may also include the meaning of "at least one sample", respectively.

The term "static" as well as any reference to velocities are in relation to world coordinates, unless otherwise indicated. Moreover, the lengths of the vectors illustrated are merely for indicative purposes only and should not to be construed as limiting.

It should be noted that the term "circular" as well as grammatical variations thereof as used herein refers to any closed or infinite path.

The term "handling" with respect to samples as used herein as well as grammatical variations thereof may refer to the performance of at least one of the following tasks at least one of the following tasks: receiving, removing, providing, sorting, inspecting, conveying, guiding and aligning of samples. Each task may be performed concurrently as well as in succession with respect to at least one other task.

Figure 2A:
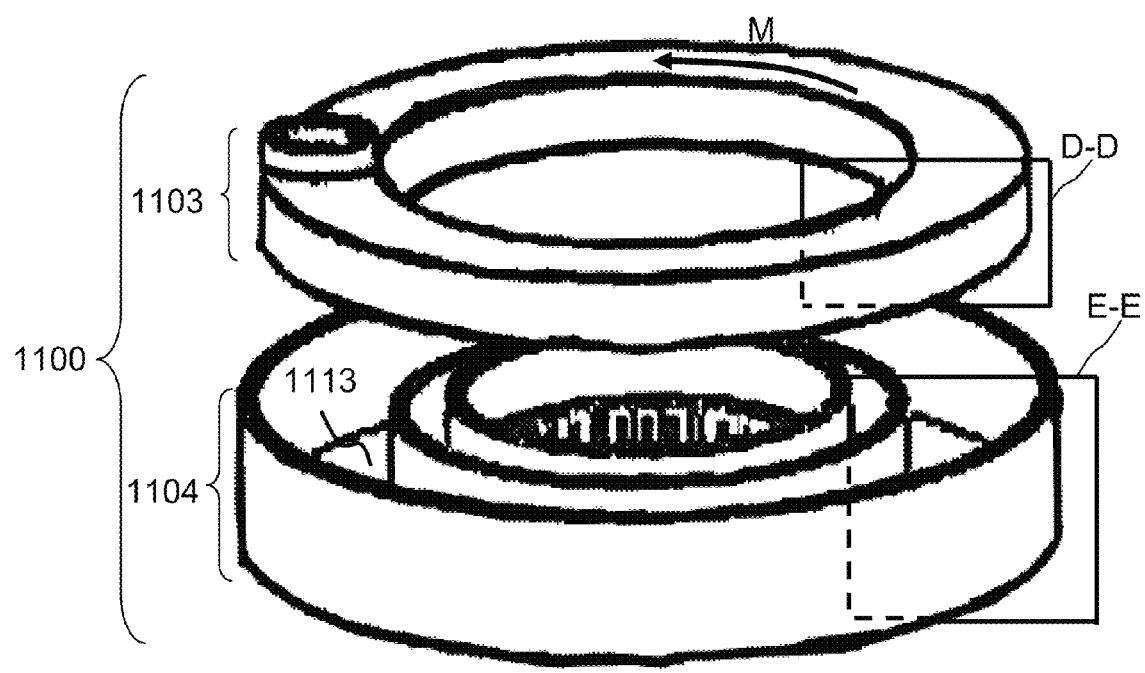
FIG. 2A is a schematic perspective view of a receptacle of the sample sorter system and device, according to an embodiment of the invention.

Referring now to FIG. 1 and to FIG. 2A, a sample sorter device and system 1000 according to embodiments of the invention includes a receptacle 1100, which may be circular and which is adapted to receive samples 1500, e.g., from at least one piping system 1210, and retain samples 1500, which may be suspended in fluid, within receptacle 1100. Receptacle 1100 is operatively coupled with a drive 1400 and with a power supply 1600 such that actuation of drive 1400 enables continuous rotation of at least one circular component of receptacle 1100. Otherwise stated, the at least one circular component is rotatably coupled to drive 1400. In turn, samples 1500 suspended in the fluid may be circularly and continuously conveyed to respective sample handling sites 1101 at a tangential speed of, e.g., maximal 5 m/sec, for example, due to a flow regime that is developed in receptacle 1100 for removal of selected samples 1500 during the rotation of receptacle 1100 via the at least one piping system 1210. The flow regime developed in receptacle 1100 may be that of a turbulent and of an at least approximate laminar flow regime. As will be outlined herein in more detail, samples 1500 can be selectively removed during rotation of receptacle 1100. Otherwise stated, samples 1500 are removable from receptacle 1100 without the need of interrupting the rotational movement of the latter.

Receptacle 1100 may be embodied by a disc or alternatively by a closed-loop annular conduit 1105 delineating a transporting route for the conveyance of samples 1500.

In embodiments of the invention, receptacle 1100 may be configured such that the entirety of receptacle 1100 is continuously rotatable by drive 1400. In some embodiments of the invention, receptacle 1100 may be configured to employ a static circular component and at least one rotatable circular component, wherein the at least one rotatable circular component can be driven by drive 1400 with respect to the static circular component such to generate a flow regime within receptacle 1100. The rotatable circular component may be embodied, for example, by one or two of the following components: an outer side wall 1111, a ground 1113 and a cover 1114 of receptacle 1100, whereas the correspondingly remaining components of receptacle 1100 embody the static circular components. For example, if ground 1113 and inner side wall 1112 are rotatable circular components, then outer side wall 1111 and if applicable cover 1114 embody the static circular components. In embodiments wherein receptacle 1100 is embodied by annular conduit 1105, then the rotatable component may be embodied additionally or alternatively by inner side wall 1112.

In some embodiments of the invention, the at least one rotatable circular component may be selectively rotatable according to an input provided by an operator via an input unit (not shown) of sample sorter device and system 1000. For example, if both ground 1113 and cover 1114 are rotatable circular components, then sample sorter device and system 1000 is adapted such that the operator may select either one or both ground 1113 and cover 1114 for rotation by drive 1400. For example, ground 1113 only may be selected by the operator for rotation whereas cover 1114 remains static, even though cover 1114 may be a rotatable circular component. Clearly, since according to embodiments of the invention receptacle 1100 may feature alternative combinations of static circular and rotatable circular components, the operator may correspondingly select various combinations of rotatable circular components for rotation by drive 1400.

Figure 2B:
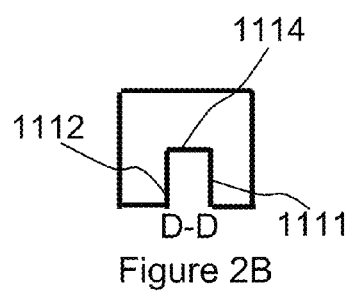
FIG. 2B is a schematic cross-sectional view of the upper part of the receptacle of FIG. 2A through plane D-D.
Figure 2C:
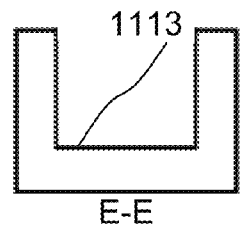
FIG. 2C is a schematic cross-sectional view of the lower part of the receptacle of FIG. 2A through plane E-E.

In addition to FIG. 2A, further reference is now made to FIGS. 2B and 2C. In the embodiment exemplified in FIG. 2A, receptacle 1100 includes an upper part 1103 and a lower part 1104, wherein upper part 1103 may be adjusted (e.g., seated) within lower part 1104, in a slidable manner, wherein the edges of the side walls of upper part 1103 may optionally slidably engage with ground 1113 of lower part 1104. Thusly configured, ground 1113 of lower part 1103, and outer side wall 1111, inner side wall 1112 and optionally cover 1114 of upper part 1104 may come into contact with fluid contained in receptacle 1100. Either one or both upper part 1103 or lower part 1104 are rotatable by drive 1400. Considering for example rotation of upper part 1103 only, then ground 1113 remains static whilst outer side wall 1111, inner side wall 1112 and cover 1114 of upper part 1103 are rotated and propel the fluid. Alternatively, rotation of lower part 1104 only, results in that fluid contained in receptacle 1100 becomes propelled by ground 1113 only. Clearly, the rotation of both upper part 1103 and lower part 1104 causes fluid contained in receptacle 1100 to become propelled by ground 1113, outer side wall 1111, inner side wall 1112, and optionally by cover 1114.

Reference is now made to FIG. 3A, FIG. 3B, FIG. 4A and FIG. 4B. If receptacle 1100 contains fluid, the rotation of the at least one circular component causes fluid molecules that are in contact with inner surfaces of receptacle 1100 to become subjected to translation or adhesive forces. In turn, fluid molecules that are not in direct contact with inner surfaces of receptacle 1100 may become subjected to shear forces. Therefore, the rotational movement of a circular component of receptacle 1100 generates a flow regime therein. In some embodiments, receptacle 1100 may be devised and operatively coupled with drive 1400 such that the flow regime generated in receptacle 1100 due to the actuation of drive 1400 is an at least approximately laminar flow regime. Correspondingly, the Reynolds number for the flow regime generated in receptacle 1100 may not exceed, for example, maximal 2300. It should however be noted that in some embodiments the flow regime generated in receptacle 1100 may be turbulent, or sometimes turbulent and sometimes laminar during the rotation of receptacle 1100. For example, samples 1500 may be conveyed along a closed path within receptacle 1100 due to the development of non-laminar (turbulent) flow, if the diameter of samples 1500 equals at least half the hydraulic diameter of annular conduit 1105. Rotating a circular component of receptacle 1100 having given geometric properties at a speed such to generate turbulent flow may result in an increased conveyance speed of samples 1500 compared to the conveyance speed attained if laminar flow was generated in the same receptacle 1100. Correspondingly, rotating a circular component of receptacle 1100 such to generate turbulent flow may in some embodiments be preferred over laminar flow. The maximal tangential velocity $V_{max}$ of the rotating circular component of receptacle 1100 may correspond or equal the maximal tangential velocity of the fluid. Therefore, in order to attain an at least approximate laminar flow regime (i.e. to keep the flow of fluid in receptacle 1100 nonturbulent) the maximal tangential velocity $V_{max}$ may not exceed 2.3 m/sec, considering a cross-sectional area for annular conduit 1105 of at least approximately $1.5 \times 1.5$ mm² and assuming that the fluid contained by receptacle 1100 is water or water-based (e.g., water containing salt or nutrients) or any other fluid having about the same viscosity as water. It should be noted that in some applications fluids that are not water or not based on water may be employed such as, for example, oil for some beads. Employing fluids that are not based on water would require determining $V_{max}$ accordingly to obtain the desired laminar and/or turbulent flow regime.

Considering a radius of, e.g., 30 mm, the rotating component of receptacle 1100 may rotate in embodiments of the invention, at a speed of for example, maximal, 273 rounds per minutes (RPM), which results in a maximal tangential fluid velocity $V_{max}$ of 2.3 m/sec to obtain a Reynolds number of maximal 2300 for samples having a cross-sectional area of $1.5 \times 1.5$ m². In alternative embodiments of the invention, the rotating component of receptacle 1100 may rotate at a speed of, for example, about maximal 180 RPM, thus obtaining a maximal tangential fluid velocity $V_{max}$ of about 0.66 m/sec. The corresponding Reynolds number may thus be maximal 2300 and the flow therefore considered laminar. In yet alternative embodiments of the invention, the rotating component of receptacle 1100 may rotate at a speed of about maximal 50 RPM. In a yet other embodiment, receptacle 1100 may be configured and be rotatably driven such that a turbulent flow regime is developed therein.

In some embodiments, the inner surfaces of receptacle 1100 may be devised to be sufficiently smooth and optionally flush with one another other such to reduce the likelihood of generating turbulence in receptacle 1100. Additionally or alternatively, inner wall structures of receptacle 1100 may be devised such to increase the speed-responsiveness of the fluid with respect to a change in the speed of rotational movement of receptacle 1100. Annular conduit 1105 may for example employ a drag-increaser like, e.g., at least one protrusion 1106 that is protruding inwardly into annular conduit 1105 to increase drag between the rotating walls of annular conduit 1105 and the fluid contained in the latter, thus overcoming inertion of the fluid quicker compared to the time required to overcome the inertion if no drag-increasers were employed.

In an embodiment of the invention, sample sorter device and system 1000 is adapted such that receptacle 1100 may be completely filled with fluid even during rotation of any of the circular components of receptacle 1100. This may be accomplished, for example, by continuous or selectively providing an inflow of fluid to receptacle 1100 such to generate an overflow of fluid from receptacle 1100 which may be drained, for example, over the upper edge of outer side wall 1111. If cover 1114 is present, the fluid may be drained through the interspace between cover 1114 and any one of outer side wall 1111 and inner side wall 1112 and/or via any suitable process-piping and/or waste-piping, which may be outlined in further detail below. By providing a continuous inflow of fluid into receptacle 1100, a possible outflow of fluid from receptacle 1100, e.g., via the at least one piping system 1210 may be compensated for, wherein such an outflow occurs for example when selectively removing samples 1500 suspended in fluid from receptacle 1100. In some embodiments, to avoid induced flow when providing samples 1500, the liquid fluid level in receptacle 1100 is kept constant by removing the amount of liquid which is inserted.

As is schematically illustrated in FIGS. 3A, 3B, 4A and 4B, sample sorter system 1000 may be adapted to generate in respective embodiments of the invention the generation of various flow regimes within receptacle 1100, wherein the flow regimes may in some embodiments be at least approximately laminar. Although the flow regimes schematically illustrated herein feature either a convex or concave flow profile, this should by no means to be construed as limiting. Accordingly, sample sorter device and system 1000 may thus also be adapted to generate alternative flow profiles than the ones schematically illustrated in FIGS. 3A, 3B, 4A, 4B and 4C. For example, circular components of receptacle 1100 may be rotated such to generate linear or turbulent flow profiles (not shown).

Figure 3A:
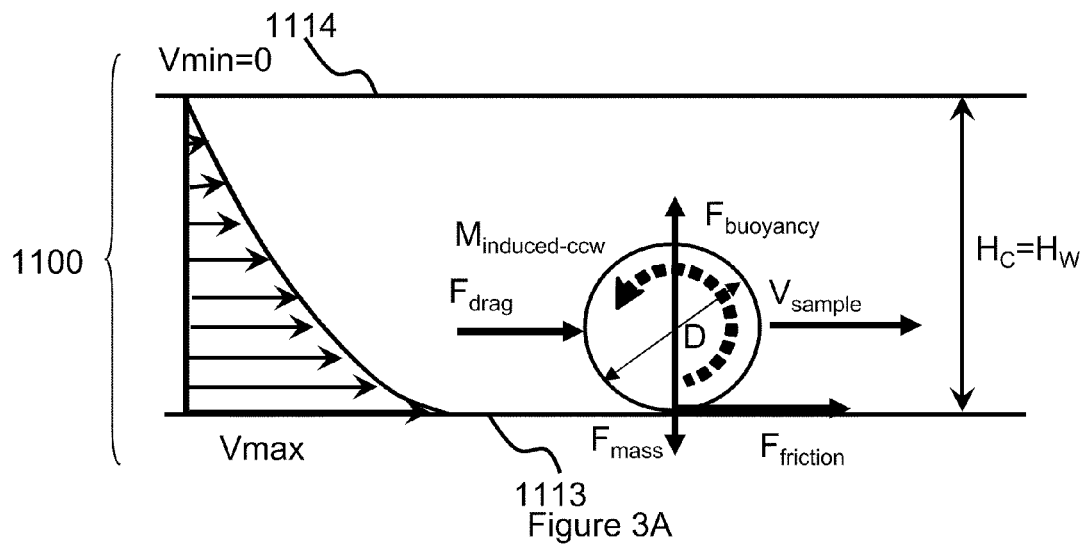
FIG. 3A is a schematic cross-sectional side view illustration along B-B of a flow profile in the receptacle according to an embodiment of the invention.

Rotatably driving ground 1113 while cover 1114 remains static generates a flow profile as schematically illustrated in FIG. 3A. It should be noted that a principally similar flow profile may be generated if in addition to ground 1113 either one or both outer side wall 1111 or inner side wall 1112 are being rotatably driven at an angular speed that is equal or lower than the angular speed of ground 1113 while cover 1114 remains static. As can readily be seen, the maximal fluid velocity $V_{max}$ corresponds to the maximal velocity of the circular component of receptacle 1100 and wherein the minimal fluid velocity $V_{min}$ corresponds to the velocity of the fluid at its upper surface. If receptacle 1100 includes cover 1114, $V_{min}$ may be equal to zero for $H_c = H_w$, wherein $H_c$ denotes the height of the receptacle and Hw the height of the fluid level. That is, due to the adhesion of the fluid's upper surface molecules with static cover 1114.

The flow regime generated by the rotation of at least one circular component of receptacle 1100 causes a corresponding propelling drag force $F_{drag}$ to act onto samples 1500. Moreover, since the density of samples 1500 may be higher than the fluid density, the corresponding force $F_{mass}$ of samples 1500 exceeds the buoyancy force $F_{buoyancy}$. As a consequence, samples 1500 are directly engaging with ground 1113 and are thus subjected to friction forces. Thus, a rotational movement of ground 1113 in embodiments of the invention causes the conveyance of samples 1500 by propelling friction force $F_{friction}$ and propelling drag force $F_{drag}$. In turn, samples 1500 are conveyed along a circular path delineated by receptacle 1100, wherein the velocity $V_{sample}$ of samples 1500 corresponds to the propelling drag force $F_{drag}$ and propelling friction force $F_{friction}$ to which samples 1500 are subjected to. It should be noted that besides a tangential component, $V_{sample}$ may also have radial component which may be effected, for example, by static friction forces between samples 1500 and ground 1113 and/or by outer side wall 1111 and/or propelling centrifugal forces (not shown), such that samples 1500 are circularly conveyed within receptacle 1100.

Clearly, the size of propelling drag force $F_{drag}$ depends on the angular velocity or RPM of receptacle 1100, and propelling friction force $F_{friction}$ depends, inter alia, on the density of samples 1500, and the nature of the surfaces of ground 1113 and samples 1500. Due to $F_{mass}$ and the propelling friction force $F_{friction}$ acting on samples 1500, rotational movement of ground 1113 may in turn induce a rotational movement of samples 1500, as is schematically illustrated with arrow $M_{induced-ccw}$. However, propelling friction force $F_{friction}$ and/or $F_{mass}$ should be such that the countermovement of samples 1500 generated by counterclockwise torque $M_{induced-ccw}$ is overcompensated to obtain $V_{sample} > 0$.

Figure 3B:
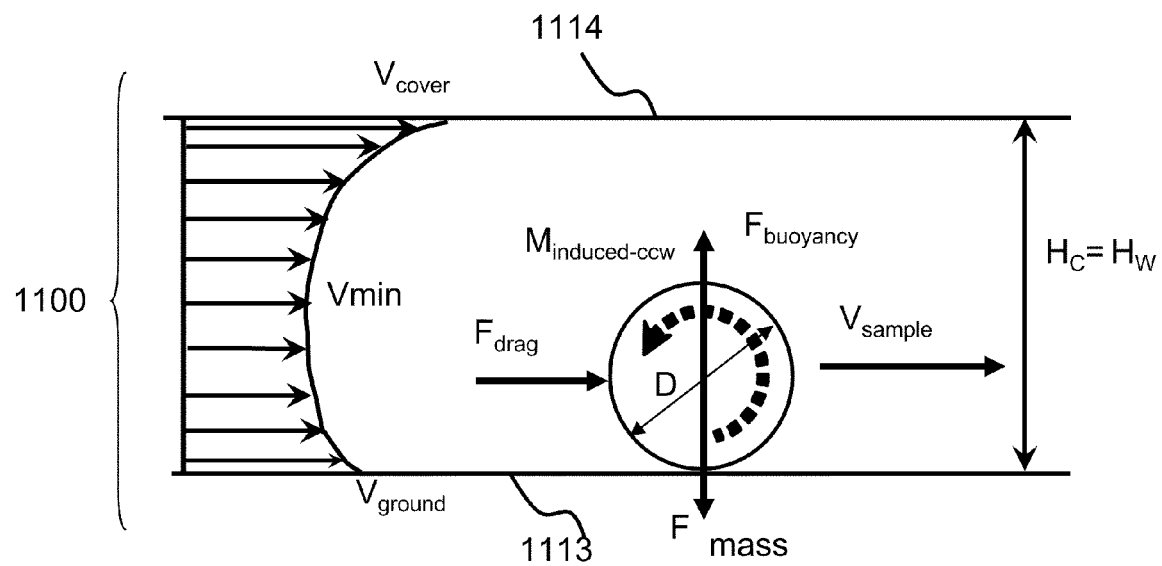
FIG. 3B is a schematic cross-sectional side view illustration along B-B of a flow profile in the receptacle according to another embodiment of the invention.

Additionally referring to FIG. 3B, sample sorter device and system 1000 may be adapted such that both ground 1113 and cover 1114 can be rotatably driven by drive 1400, while outer side wall 1111 and/or inner side wall 1112 have an angular velocity that is slower or equals to zero (i.e. are stationary/static). Thusly configured, a corresponding concave flow profile may be generated. It should be noted that the angular velocity ground 1113 and cover 1114 may be equal or differ from one another in respective embodiments of the invention. However, the resulting corresponding forces diagram acting on samples 1500 may be in principle remain the same as the diagram illustrated in FIG. 3A, except for the lengths of the vectors which may have to be altered accordingly. It should be noted that in some embodiments of the invention, $V_{ground} = V_{cover} = V_{max}$.

In some embodiments of the invention, sample sorter device and system 1000 may be adapted such that outer side wall 1111 and inner side wall 1112 remain static, or may be rotated at an angular speed that is lower than the angular speed of ground 1113 and cover 1114.

Figure 4A:
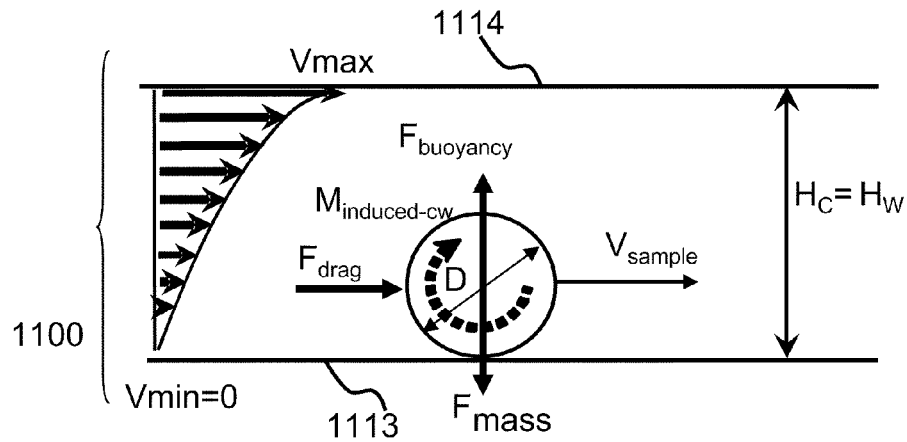
FIG. 4A is a schematic cross-sectional side view illustration along B-B of a flow profile in the receptacle according to a yet alternative embodiment of the invention.

Referring now to FIG. 4A, ground 1113 and optionally outer side wall 1111 and/or inner side wall 1112 may in some embodiments of the invention remain static, while cover 1114 is rotatably driven by drive 1400 such that the corresponding flow regime may have its maximal velocity $V_{max}$ where the fluid interacts directly with cover 1114. The ensuing propelling drag force $F_{drag}$ may induce a clockwise torque $M_{induced-cw}$ acting on samples 1500, which in turn may result in a clockwise movement of the latter such that samples 1500 may self-rotate on ground 1113 in the direction of $V_{sample}$.

In the embodiment schematically illustrated in FIG. 4A, wherein ground 1113 remains static, samples 1500 may only be subjected to propelling drag force $F_{drag}$ and not to propelling friction forces $F_{friction}$ that would otherwise be exerted on sample 1500 by the rotation of ground 1113. Otherwise stated, conveyance of samples 1500 may be performed in a so-called frictionless manner in sample sorter device and system 1000 by the rotation of cover 1114 only. It should be noted that the term "frictionless" as used herein does not necessarily mean the complete absence of of friction forces on samples 1500, but only refers to a reduction or absence of propelling friction forces.

It should further be noted that frictionless conveyance may also refer embodiments wherein ground 1113 remains static, whereas any of outer side wall 1111 and/or inner side wall 1112 and/or cover 1114 rotate in the same direction with respect to ground 1113, although samples 1500 may be frictionally driven by either one or both rotating side walls 1111 and 1112.

The maximal fluid velocity $V_{max}$ that is attained when rotating cover 1114 only is at the interface between the fluid and the rotating cover 1114. The corresponding flow profile may thus increase to a maximum from ground 1113 to cover 1114.

Figure 4B:
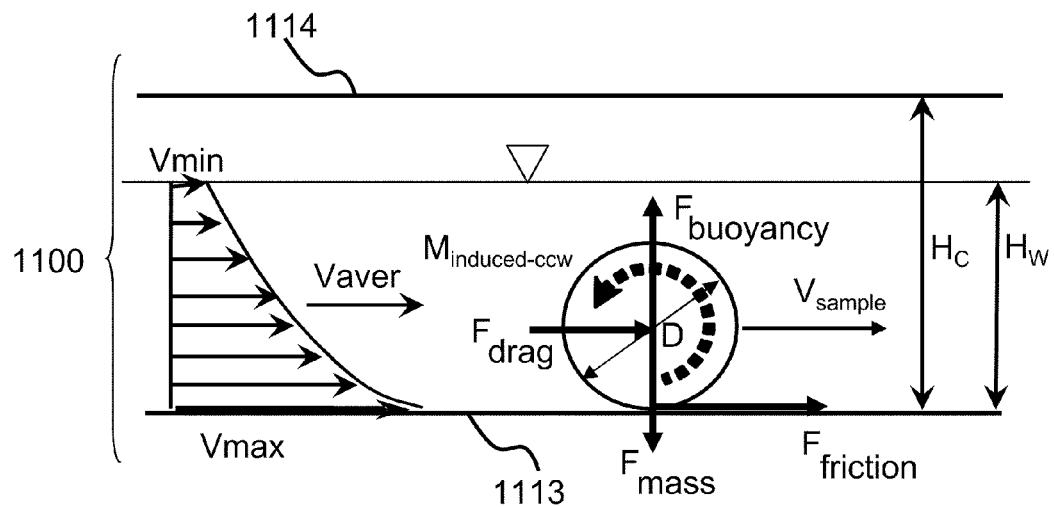
FIG. 4B is a schematic cross-sectional side view illustration along B-B of a flow profile in the receptacle according to another alternative embodiment of the invention.
Figure 4C:
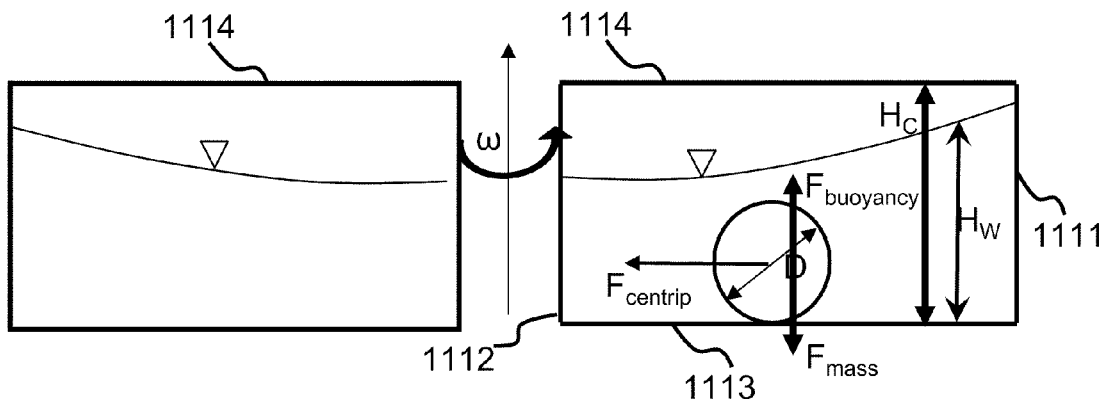
FIG. 4C is a schematic cross-sectional side view illustration of the receptacle along line A-A, according to an embodiment of the invention.
Figure 5A:
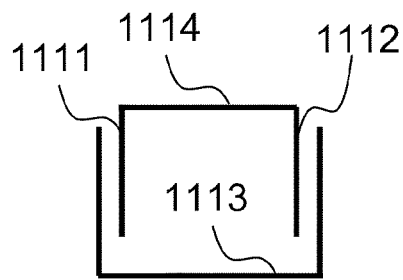
FIGS. 5A to 5F are schematic cross-sectional front view illustrations of the receptacle along C-C according to respective embodiments of the invention.
Figure 5B:
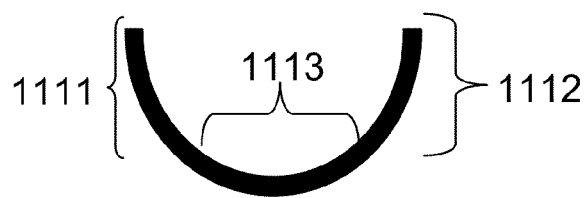
Figure 5C:
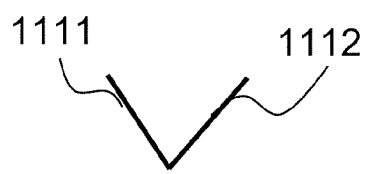
Figure 5D:
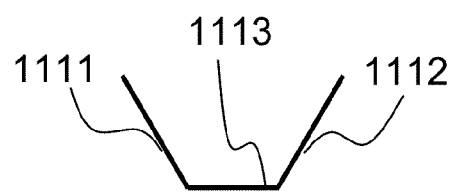
Figure 5E:
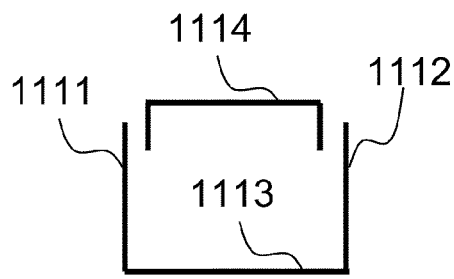
Figure 5F:
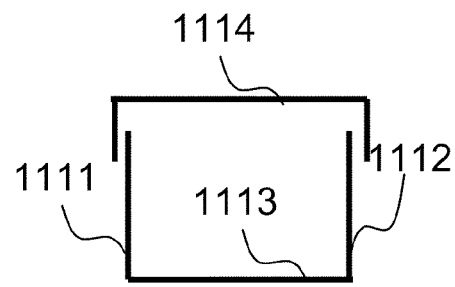

Referring now to FIGS. 4B and 4C, receptacle 1100 may be adapted to circularly convey samples 1500 while not being completely filled with fluid. Rotatably moving ground 1113 may thus lead to a flow profile as schematically illustrated in FIG. 4B. A corresponding force diagram for view A-A is schematically illustrated in FIG. 4C.

In an embodiment of the invention, the flow profile that can be generated by sample sorter device and system 1000 in receptacle 1100 may be such, so that any self-rotation of samples 1500 relative to ground 1113 by rolling and/or sliding is reduced or eliminated. Thus, friction forces that might ensue due to the self-rotation of samples 1500 relative to ground 1113 are reduced accordingly or eliminated. Correspondingly, the area of the surface regions of samples 1500 that frictionally interact directly with ground 1113 is reduced or may be kept at a minimum. Therefore, samples 1500 are subjected less to potentially abrading friction forces, which may be damaging to samples 1500.

To obtain a self-rotationless movement of samples 1500, at least ground 1113 is rotatably moved such that torques to which samples 1500 may be subjected cancel each other out so that samples 1500 are subjected to a total torque of $M = 0$.

It should be noted that although samples 1500 are herein illustrated as an $F_{mass} > F_{buoyancy}$ this is not to be construed as limiting. Accordingly, receptacle 1100 may be adapted to convey samples 1500 for which $F_{mass} \leq F_{buoyancy}$.

Referring now to FIGS. 5A, 5B, 5C, 5D, 5E and 5F, various possible cross-sectional shapes of annular conduit 1105 viewed from A-A (cf. FIG. 1) are exemplified. It should be noted that these cross-sectional shapes for annular conduit 1105 are not to be construed as limiting and that annular conduit 1105 may have alternative cross-sectional shapes. In some embodiments of the invention, the cross-sectional shape may alter along the diameter of annular conduit 1105 in manner that facilitates the successive alignment of samples 1500 therein.

Reverting now again to FIG. 1, the at least one piping system 1210 may be embodied, for example, by a supply-piping 1210A, and a sample-removal piping embodied by, e.g., a process-piping 1210B and a waste-piping 1210C, which respectively include supply-interconnection 1211A, process-interconnection 1211B and waste-interconnection 1211C operatively communicating with receptacle 1100.

Sample sorter device and system 1000 is adapted to provide receptacle 1100 with samples 1500 through supply-piping 1210A from a sample source site 1215A via supply-interconnection 1211A. In some embodiments, supply-piping 1210A may be shaped like a funnel, i.e., tapered towards receptacle 1100 to facilitate the supply of samples 1500. The sample source may be any of the following: an apparatus (e.g., a continuous feeder), a system and an operator. Accordingly, the sample source may be provided in a Barth's buffer or in any other fluid by feeding with a steady flow from a previous fluidic system such as, for example, a rough sorter like, e.g., a twin mesh size sorter.

In some embodiments, receptacle 1100 may include fluid such that unsuspended samples 1500 provided to receptacle 1100 become suspended into the fluid contained in the latter. In some embodiments, samples 1500 may already be provided in the suspension of a fluid to receptacle 1100. In any event, supply-piping 1210A may be adapted to provide receptacle 1100 with both suspended and unsuspended samples 1500. Accordingly, receptacle 1100 is adapted to receive and to circularly convey suspended and unsuspended samples 1500. It should be noted that term "suspended samples" refers to samples that are suspended in a fluid. Correspondingly, the term "unsuspended samples" relates to samples that are not suspended in a fluid. Unsuspended samples may for example refer to samples 1500 that are embodied by dry beads which may be inserted or dropped into receptacle 1100.

Process-piping 1210B employs components that are adapted to guide samples 1500 from receptacle 1100 to a process-site 1215B for further processing; and waste-piping 1210C employs components that are adapted to guide samples 1500 from receptacle 1100 to a waste-site 1215C (not shown). Process-site 1215B may be embodied, for example, by a microinjection apparatus, an examination apparatus, vials, a robotic platform distributing extracted samples 1500 into the individual wells of a multiwellplate, an operator or any entity facilitating further processing of samples 1500 received by or passing through process-interconnection 1211B. It should be noted that although process-interconnection 1211B and waste-interconnection 1211C are schematically illustrated as being separate from each other, this should not be construed as limiting. In some embodiments for example, process-interconnection 1211B and waste-interconnection 1211C may be embodied by the same receptacle-piping-interconnection. Accordingly, receptacle 1100 may communicate via a single receptacle-piping-interconnection with both process-piping 1210B and waste-piping 1210C such that samples 1500 are selectively deliverable on demand to waste-site 1215C and process-site 1215B.

Sample sorter device and system 1000 additionally employs an examination-site 1310 that is located after supply-interconnection 1211A and before both process-interconnection 1211B and waste-interconnection 1211C with respect to the rotation of direction M. The location of examination-site 1310 is defined by the location or section during which samples 1500 may be examined or inspected by sensor 1300. In embodiments of the invention, sample examination-site 1310 is located before both process-interconnection 1211B and waste-interconnection 1211C, but after supply-interconnection 1211A in relation to the rotation direction of receptacle 1100. Accordingly, samples 1500 provided to receptacle 1100 first pass examination-site 1310 prior to being circularly conveyed to process-interconnection 1211B and waste-interconnection 1211C.

The outcome of the examination determines which of samples 1500 may be provided to process-site 1215B and which may be provided to waste-site 1215C. More specifically, sensor 1300 is operatively coupled with process-piping 1210B and with waste-piping 1210C in a way enabling process-piping 1210B and waste-piping 1210C to be operable according to inputs received from sensor 1300 such that samples 1500 are selectively deliverable on demand to process-site 1215B and waste-site 1215C while receptacle 1100 continues rotating. If for example sensor 1300 determines that the inspected samples 1500 are usable for further processing, process-piping 1210B and waste-piping 1210C may be set such that the inspected samples 1500 are delivered to process-site 1215B. Conversely, if for example sensor 1300 determines that the inspected samples 1500 are unusable for further processing, process-piping 1210B and waste-piping 1210C may be set such that the inspected samples 1500 are delivered to waste-site 1215C. In embodiments of the invention, the default positions for process-piping 1210B and/or waste-piping 1210C may be "open" or "closed". For example, waste-piping 1210C may be open by default, whereas process-piping 1210B may be closed by default. As a consequence, unless an otherwise indicative input is provided by sensor 1300, samples 1500 are provided to waste-site 1215C. Conversely, if process-piping 1210B is in a corresponding embodiment open by default and waste-piping 1210C is closed by default, then samples 1500 are delivered by default to process-site 1215B. In some embodiments of the invention, both process-piping 1210B and waste-piping 1210C are closed by default. Thusly configured, samples 1500 are circularly conveyed by receptacle 1100 and stored in sample sorter system 1000 until either one of process-piping 1210B and waste-piping 1210C is being set to open in response to a corresponding input received from, e.g., sensor 1300. In some embodiments, both process-piping 1210B and waste-piping 1210C may be open by default and the input provided by sensor 1300 may activate the closure of process-piping 1210B and waste-piping 1210C.

According to some embodiments of the invention, supply-piping 1210A may be operatively coupled with sensor 1300 such that supply-piping 1210A may be opened or closed to receptacle 1100 according to corresponding inputs received from sensor 1300. For example, sensor 1300 may determine that the number of samples 1500 conveyed by receptacle 1100 exceeds a predetermined threshold. In turn, sensor 1300 may provide supply-piping 1210A with an input command to close supply-piping 1210A.

According to some embodiments of the invention, the last state of supply-piping 1210A and/or process-piping 1210B and/or waste-piping 1210C may be retained until the subsequent input provided, e.g., according to a time limit from a processor (not shown); by sensor 1300 which may be embodied, for example, by cameras 1301 and 1302 and/or by a light barrier; and/or by any other suitable device and/or by the operator.

Figure 6:
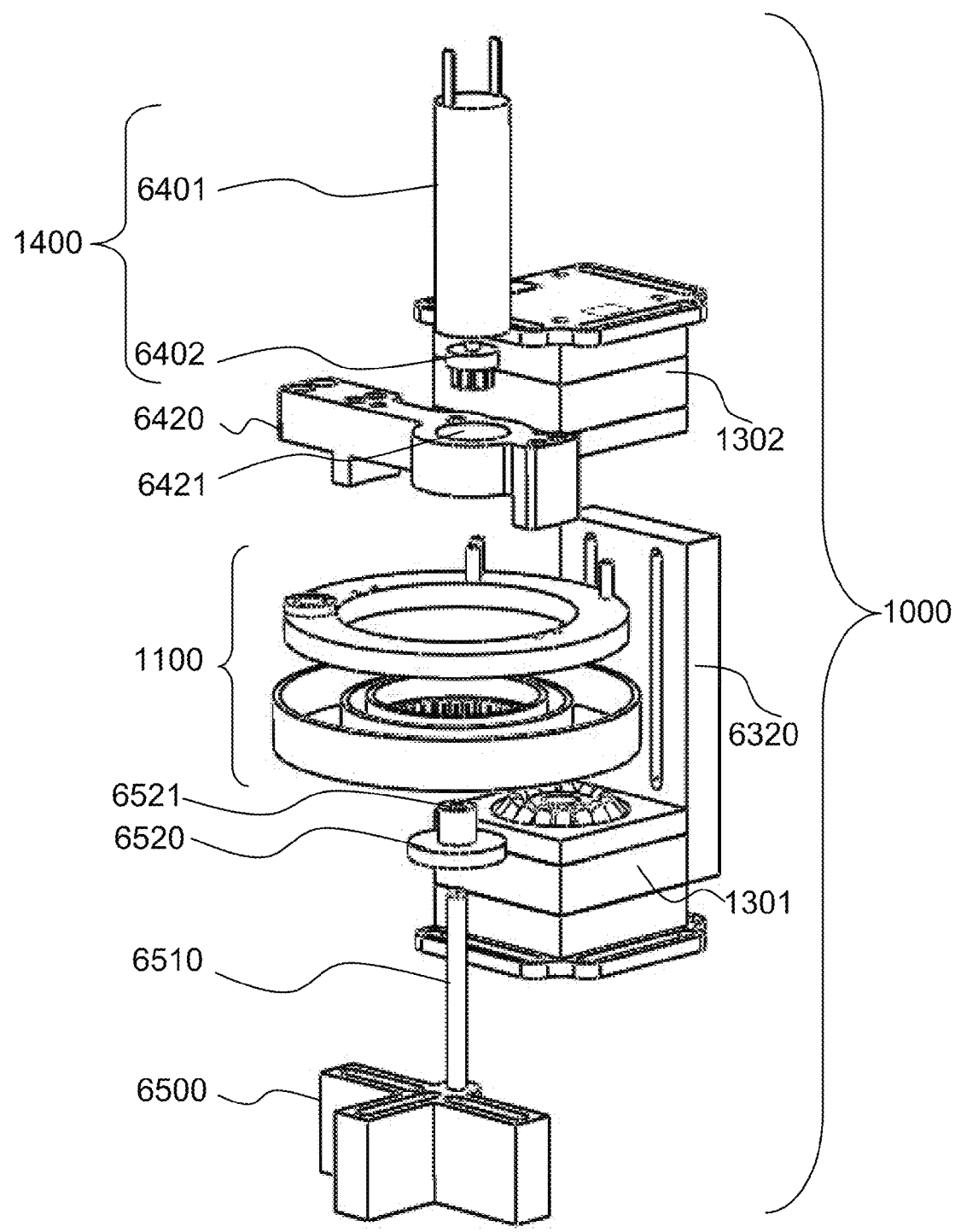
FIG. 6 is a schematic perspective exploded view of the sample sorter system and device, according to an embodiment of the invention.
Figure 7:
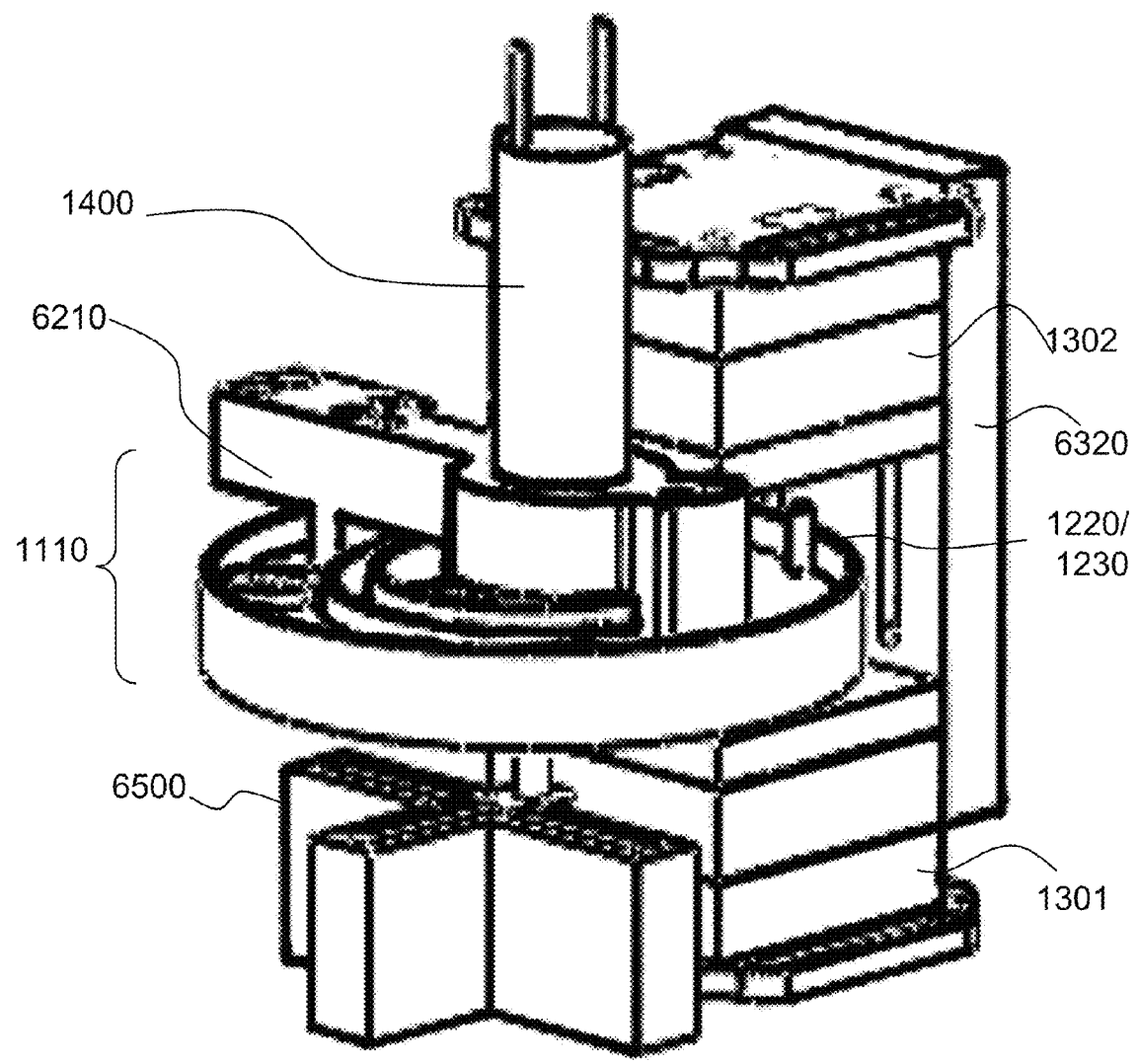
FIG. 7 is a schematic perspective assembly view of the sample sorter system and device, according to an embodiment of the invention.

Additionally referring now to FIG. 6 and FIG. 7, sensor 1300 may be embodied, for example, by a visual examination sensor and/or a capacitance-based sensor and/or a light barrier and/or a fluorescence-based sensor, wherein sensor 1300 is adapted to determine whether samples 1500 are present in receptacle 1100, and/or whether they are passing examination-site 1310 as well as the characteristics of certain parameters of samples 1500. A non-exhaustive list of such parameters includes volume; morphological complexity; cell pigmentation; viability as well as other chemical and/or physical and/or biological parameters. In particular, a camera system may be employed for determining the characteristics of samples.

In an embodiment of the invention, sensor 1300 may for example be adapted to perform imaging of a plurality of differently oriented surfaces of samples 1500 passing examination-site 1310, wherein the region-of-interest that is imageable may be, for example, at least 1.5-10 times the diameter of samples 1500. Sensor 1300 may for example be implemented by two cameras 1301 and 1302 enabling two-sided imaging of respective surfaces of samples 1500, wherein the surfaces may be opposite and optionally complementary to one another. Accordingly, these two cameras 1301 and 1302 may be positioned in front of opposite surfaces of samples 1500. Both first camera 1301 and second camera 1302 are responsively coupled with process-piping 1210B and waste-piping 1210C. Employing a plurality of cameras may in particular be useful for the analysis of samples 1500 that are opaque such as, for example, *Xenopus laevis oocytes*.

First camera 1301 and second camera 1302 may be positioned with respect to receptacle 1100 such that the entire surface of samples 1500 conveyed therein is imageable. Additionally or alternatively, a plurality of images of samples 1500 may be acquired by, e.g., first camera 1301 and/or second camera 1302, until the entire surface of samples 1500 is imaged. In some embodiments, first camera 1301 and/or second camera 1302 may be controllable and moveable mounted and coupled with drive 1400 such to track samples 1500 by change of position.

In some embodiments, the part of the surface that may be imaged by first camera 1301 (hereinafter: front surface) may partially overlap the part of the surface that may be imaged by second camera 1302 (hereinafter: rear surface). Accordingly, the ROI of first camera 1301 may differ from the ROI of second camera 1302. In some embodiments, the optical axis $Z_{1302}$ of second camera 1302 may at least approximately coincide with the optical axis $Z_{1301}$ of first camera 1301.

The camera system described herein may be adapted to discard information with respect to surfaces being imaged in overlap. The camera system may be employ any image processing algorithm, e.g., as known in the art.

Considering for example that receptacle 1100 in an embodiment is transparent to the imaging wavelengths, image information that is obtainable by first camera 1301 may be at least complementary to the image information that is obtainable by second camera 1302, and vice versa. For example, as is schematically illustrated in FIGS. 6 and 7, in an embodiment wherein receptacle 1100 is transparent to the imaging wavelength, first camera 1301 may positioned above receptacle 1100 and second camera 1302 may be positioned below receptacle 1100 and opposite to first camera 1301 such that optical axes $Z_{1301}$ and $Z_{1302}$ are parallel, or alternatively aligned to coincide with each other. Thusly configured, the front surface and the at least complementary rear surface of samples 1500 may be imaged by first and second camera 1301 and 1302, respectively, and the front surface and the rear surface being imaged may together make up the entire surface of samples 1500. By employing the two-sided imaging outlined herein, features that remain non-imageable by first camera 1301 are imageable by second camera 1302, and vice versa. Such features may include, for example, a cluster of cells that are adhesively coupled to the rear surface of sample 1500 in a manner such that the cluster is non-imageable by first camera 1301. However, by employing second camera 1302, the cluster becomes imageable.

In an embodiment of the invention, sensor 1300 may additionally embody a distance measurer that is adapted to determine the distance between two successive samples 1500. For example, either one or both first camera 1301 and second camera 1302 may determine whether the distance between two neighboring samples 1500 conveyed in receptacle 1100 is large enough such to determine characteristics of a selected sample 1500 and to enable timely removal of a selected sample 1500 only such that a non-selected sample 1500 remains in receptacle 1100. This may for example be accomplished by determining whether the imaged ROI captured more than one sample 1500, and if yes, whether the distance between two successive samples 1500 exceeds a certain distance-threshold, which may be set according to a reference diameter respective of samples 1500. For instance, the distance-threshold may be set to be, e.g., 1, or 1.5 times the average or median diameter of, e.g., *Xenopus Oocytes*. Alternatively, the distance-threshold may be set adaptively according to the diameters of samples 1500 currently being imaged by, e.g., first camera 1301. The threshold may for example be determined according to an average of the currently imaged samples 1500 or according to a sample 1500 that is most centered in the ROI. If the distance-threshold between two successive samples 1500 exceeds by, e.g., a factor of 1, 1.5, 2, 3, 4, 5, 6, 7 or 8 the reference diameter, then one of the successively conveyed and in the ROI captured samples 1500 may be selected and second camera 1302 may then in addition be set into operation for determining the characteristics of the selected sample 1500. It should be noted that the sequence of operation of first camera 1301 and second camera 1302 as outlined herein is for exemplary purposes only. Accordingly, second camera 1302 may be initially operated and only then first camera 1301, or both first camera 1301 and second camera 1302 may be employed concurrently in some embodiments of the invention, e.g., for mutual verification and/or comparison of the gathered information.

It should further be noted that in some embodiments of the invention, a sample 1500 may be selected prior to determining whether the distance to neighboring samples is large enough. In an embodiment of the invention, only first camera 1301 may initially be employed for determining the characteristics of selected sample 1500, whereby second camera 1302 may only then be employed if the characteristics determined by first camera 1301 meet the predetermined at least one criterion, or vice versa. In another embodiment of the invention, both first camera 1301 and second camera 1302 may be employed concurrently to determine the characteristics of the selected sample 1500. In any event, only if the information respective of the selected sample 1500 gathered both by first camera 1301 and second camera 1302 meets the at least one criterion, the selected sample 1500 may be provided to process-piping 1210B. Otherwise stated if the information gathered by either one or both first camera 1301 and second camera 1302 does not meet the at least one criterion, the selected sample 1500 may be provided to waste-piping 1210C, or may be conveyed further within receptacle 1100 without being provided to process-piping 1210B.

According to an embodiment of the invention, sensor 1300 may be set into operation upon receiving a suitable input which may be provided, e.g., by the operator or from another sensor (not shown) such as, for example, an optical or mechanical motion sensor) that is operatively coupled with sensor 1300, and the like. The other sensor may in some embodiments be employed by, e.g., process-site 1215B and/or waste-site 1215C.

In some embodiments, as is schematically illustrated in FIG. 1, the optical axis $Z_{1301}$ of first camera 1301 and the optical axis $Z_{1302}$ of second camera 1302 aligns with a radial vector of R of receptacle 1100 originating from the geometric center-point O of the latter and optionally coincide.

In some embodiments of the invention, receptacle 1100 may be configured such that individual samples 1500 are therein alignable in succession to ensure that only one sample 1500 at a time is positioned in front of process-valve 1212B and waste-valve 1212C and for removal thereby. For example, the width W of receptacle 1100 embodied by annular conduit 1105 may for example be such that at a given cross-section of annular conduit 1105 only one sample 1500 is positionable between outer side wall 1111 and inner side wall 1112. Otherwise stated, in some embodiments of the invention the width of annular conduit 1105 for example may only be slightly larger than the maximum diameter of samples 1500 and may be, for example, 1.1 to 1.5 times larger than the diameter of samples 1500 provided to receptacle 1100. If for example samples 1500 are embodied by *Xenopus laevis oocytes*, the largest thereof having a diameter of e.g., 1.3 mm, then the width W of annular conduit 1105 may be, for example, maximal 1.5 mm and the height, e.g., 2 mm. For samples 1500 having a diameter of about, e.g., 20 μm, the channel width W and height should not exceed, e.g., 30 μm. In some embodiments of the invention, receptacle 1100 may have a cross-section C-C that is narrowing or tapering towards ground 1113 such that by rotation of receptacle 1100 samples 1500 are being lined up in succession within receptacle 1100.

In order to enable the successive alignment for a variety of types of samples 1500 in receptacle 1100, the width W of annular conduit 1105 may be automatically or manually adjustable. For example, receptacle 1100 may be adapted such that inner side wall 1112 having a first radius is replaceable by another inner side wall 1112 of larger or smaller radius by, e.g., the operator. Similarly, outer side wall 1111 may in some embodiments be replaceable another outer side wall 1111 of larger or smaller radius. According to some embodiments of the invention, a selected one of a plurality of replaceable annular conduits 1105 of respective different widths may be positioned in receptacle 1100. Thusly configurable, receptacle 1100 may be adjusted such that samples 1500 are aligneable in succession within annular conduit 1105.

Clearly, for a given width W, the amount of samples 1500 that can be circularly conveyed in succession in annular conduit 1105 depends on the radius of outer side wall 1111. The larger the radius, the larger is the diameter of annular conduit 1105 and the more samples 1500 are therein storable in succession. For example, if the radius of outer side wall 1111 is 31 mm, approximately 100 Xenopus oocytes can be circularly conveyed in succession in annular conduit 1105.

In addition or as an alternative to adjusting the width W of annular conduit 1105 according to the maximal diameter of samples 1500, a fluidic focusing mechanism (not shown), e.g., as known in the art may be employed in sample sorter system 1000 to successively align samples 1500 in annular conduit 1105.

The successive alignment of samples 1500 within annular conduit 1105 alone may not suffice to ensure that during the opening of process-valve 1212B and/or waste-valve 1212C only one sample 1500 will be removed at a time. The response and opening time of process-valve 1212B and/or waste-valve 1212C as well have to be timed such that not more than one sample 1500 at a time passes interconnecting ports of process-piping 1210B and waste-piping 1210C during the opening of process-valve 1212B and waste-valve 1212C, respectively. Clearly, the faster samples 1500 move within receptacle 1100, the shorter must be the response time and the opening time of process-valve 1212B and waste-valve 1212C to ensure that only a selected one of samples 1500 is removed from receptacle 1100, in the event that another sample 1500 follows the selected one at a distance that equals or is larger than the corresponding distance-threshold. A higher RPM will lead to an increase in $V_{sample}$ for samples 1500 of a given diameter. Considering for example rotating a circular component of receptacle 1100 at a an RPM such that a first sample 1500 of the type of, e.g., Xenopus Oocytes attains a tangential velocity of 5 m/sec, process-valve 1212B and waste-valve 1212C may be adapted to switch open, remove a first sample 1500 and close again within 300 microseconds. For samples 1500 having a diameter of 20 µm diameter, process-valve 1212B and waste-valve 1212C may be adapted to switch open, remove a first sample 1500 and close within 6 microseconds. Thusly configured, it is ensured that for any distance between first and second sample 1500 being equal or larger than (i.e., at least equal) the distance-threshold, only the first sample 1500, if selected, is removed from receptacle 1100. The sequence of opening, removal and subsequent closing of valves is hereinafter referred to as "switch time". Clearly, the switch time may be increased accordingly should the distance between first and second samples 1500 increase.

Considering now for example a valve having a switch time of 300 microseconds and samples 1500 moving at $V_{sample}=5$ m/sec, then Xenopus Oocytes may be removable after every, e.g., 600 microseconds when taking into account a threshold-distance of one Oocyte diameter, or a valve having a switch time of 6 miroseconds and a sample diameter of 20 µm, after every 12 microseconds a sample may be removed in an embodiment of the invention. Accordingly, 100 Xenopus Oocytes or 5000 samples 1500 with a diameter of 20 µm are removable within 60 milliseconds for example. It should be noted that in order to attain a tangential velocity of 5 m/sec for samples 1500, the corresponding tangential velocity (and thus the RPM) of receptacle 1100 have to be higher. This is due to the fact that a) the fluid is not rigidly fixed to the receptacle, but is put into motion by shear forces and cohesion forces within the liquid and b) the sample experiences other forces than the propelling fluid drag force alone.

In order to ensure timely removal of a selected one of samples 1500, the trigger time for opening and closing of process-valve 1212B and/or waste-valve 1212C has to be determined, which is based on the geometry of annular conduit 1105, the distance between examination-site 1310 and the outlet ports of process-piping 1210B and waste-piping 1210C, the velocity or speed $V_{sample}$ of samples 1500, as well as a system related delay such as the switching time (e.g., 10 ms) of the valves and computer processing time (e.g., 40 ms). Valve switching time may be determined experimentally (only once for the setup), and the computer processing time may be determined for each image processing algorithm employed.

Considering t-delay=(distance to valve outlet port)/(velocity of entity) then the following criterion has to be met with respect to t-delay to enable timely removal of a selected one of samples 1500: (t-delay)−(t-switch)−(t-processing)>0. Considering for example, a distance to valve outlet port of 6 mm and a velocity of the entity of 26 mm/sec, then the delay would be at least approximately 6 mm/26 mm/sec=0.23 sec.

In view of the aforesaid, the importance of adjusting the RPM of receptacle 1100 to the size of samples 1500 and to the switch time of process-valve 1212B and/or waste-valve 1212C is apparent. Therefore, according to some embodiments of the invention, sensor 1300 may be operatively coupled with drive 1400 such that the RPM of receptacle 1100 can be adaptively altered according to an input received from sensor 1300 and/or the operator. For example, sensor 1300 may determine the diameter of a single sample 1500 passing examination-site 1310, determine based on said determined diameter the maximal allowed RPM for the given sample 1500, determine whether a reduction in the RPM is required and if yes, provide drive 1400 with an input representing information about the required reduction in RPM such to be below the maximal allowed RPM for removal of one sample 1500 at a time by process-valve 1212B and/or waste-valve 1212C. In some embodiments, the RPM may be adjusted only after at least one revolution of receptacle 1100 and/or after a minimum number of samples 1500 pass examination-site 1310. More specifically, sensor 1300 may for example determine the diameters of samples 1500 passing examination-site 1310 during, e.g., 1, 2, or 3 revolutions of receptacle 1100, determine the value of the largest diameter and if necessary, adjust the RPM of drive 1400 and thus the RPM of receptacle 1100 accordingly. Additionally or alternatively, the RPM of drive 1400 may be adjusted only after the diameter is determined for a given number of samples 1500 by, e.g., sensor 1300.

It should be noted that although sensor 1300 is herein referred to as the unit which determines the diameter of samples 1500, an optional adjustment of the RPM of drive 1400, and characteristics of samples 1500, this should by no means be construed as limiting. Accordingly, additional or alternative processing units (not shown) and/or devices (not shown) than sensor 1300 may be employed to determine, e.g., characteristics of samples 1500 and/or an adjustment of the RPM of drive 1400, and the like.

According to some embodiments of the invention, process-valve(s) 1212B and/or waste-valve(s) 1212C may only be opened (e.g., unlocked for operation) after receiving an input which represents information that the RPM of receptacle 1100 is adjusted such to enable timely removal of a selected one of samples 1500. For example, sensor 1300 may unlock process-valve 1212B and waste-valve 1212C after receiving a feedback from drive 1400 or receptacle 1100 that the RPM is below a maximal allowed RPM limiting the removal to one sample 1500 only during the respective switch time.

By employing sensor 1300 embodying a visual examination system comprising, e.g., first camera 1301 and second camera 1302, determining the characteristics of samples 1500 is performable according to non-fluorescence based methods, i.e., in a manner which is free of fluorescence markers or labels. In addition, the sorting of samples 1500 is performable in a manner which does not require the employment of potentially lethal electrostatic charges (i.e., in an electrostatic-free manner). As a consequence, samples 1500 conveyed and sorted by sample sorter device and system 1000 may not be subjected potentially damaging and/or imperfecting fluorescence labels and electrostatic charges for analysis and sorting, respectively.

However, in some embodiments of the invention, fluorescence markers or labels may be employed, in addition or as an alternative to a visual examination system. For example, if some of the characteristics as gathered and determined by, e.g., first camera 1301 and second camera 1302 may be border-line and/or ambiguous for making a decision whether to remove the respective samples 1500 via process-piping 1210B or waste-piping 1210C, then fluorescence labels or markers together with an illumination system (e.g., a lasing system and photomultiplier) may additionally be employed for further examination of the respective border-line or ambiguous samples 1500.

According to some embodiments of the invention, the opening time of supply-valve 1212A may be limited to avoid an excess in supply of samples 1500 and thus a possible clogging of receptacle 1100. For example, the opening time of supply-valve 1212A may be clocked or synchronized in accordance with the opening of either or both process-valve 1212B and waste-valve 1212C. Additionally or alternatively, supply-valve 1212A may be operatively coupled with a sample counter (not shown) such that when the number of samples 1500 counted by the sample counter exceeds a first predetermined sample-quantity-threshold, commands to open supply-valve 1212A may be overridden such that supply-valve 1212A remains closed. Conversely, if the number of samples 1500 counted by the sample counter is below a second predetermined sample-quality-threshold, then supply-valve 1212A may be unlocked for opening and the override be cancelled. In some embodiments, a sample counter may in addition to supply-piping 1210A also be coupled with process-piping 1210B and waste-piping 1210C in a manner that enables determining the net supply of samples 1500 during subsequent time intervals. If the net supply during a certain time interval exceeds a predetermined sample-quantity-threshold, supply-valve 1212A may be provided with an input to be closed. The sample counter(s) may be embodied, for example, by a light barrier, a mechanical switch and in some embodiments, by sensor 1300. Clearly, since samples 1500 may be released or selectively removed on demand from receptacle 1100, the latter may also constitute a storage device for samples 1500 conveyed therein. Otherwise stated, samples 1500 may be stored in and circularly conveyed for an indefinite time by receptacle 1100, wherein due to the rotation of the at least one rotating component, adhesion of samples 1500 to one another is prevented or the probability thereof is at least reduced. Samples 1500 may thus repeatedly pass supply-interconnection 1211A, examination-site 1310, process-interconnection 1211B and waste-interconnection 1211C.

Referring now again to FIG. 6 and FIG. 7, first camera 1301 may in some embodiments be mechanically coupled to the bottom of a camera holder 6320 such that first camera 1301 is positioned below receptacle 1100 for visual examination of samples 1500 from below. Further, second camera 1302 may be mechanically coupled to the top of camera holder 6320 such to be positioned above receptacle 1100 for visual examination of samples 1500 from above. Accordingly, first camera 1301 may constitute a support for camera holder 6320, which itself may constitute a support for second camera 1302.

Drive 1400 includes a motor 6401 that may be operatively coupled with a gear 6402 having a certain gear ratio of, e.g., 15. Motor 6401 may be mechanically coupled to a drive holder 6420, which may be coupled to a rotary axis 6510 of a stand 6500. Gear 6402 may be held affixed in space in an opening 6421 of a drive holder 6420 such to operatively communicate with a rotating component of receptacle 1100.

The rotating component of receptacle 1100 may be supported by a bearing 6520 having an opening 6521, wherein bearing 6520 rotatably communicates via said opening 6521 with rotary axis 6510 of stand 6500.

Figure 8:
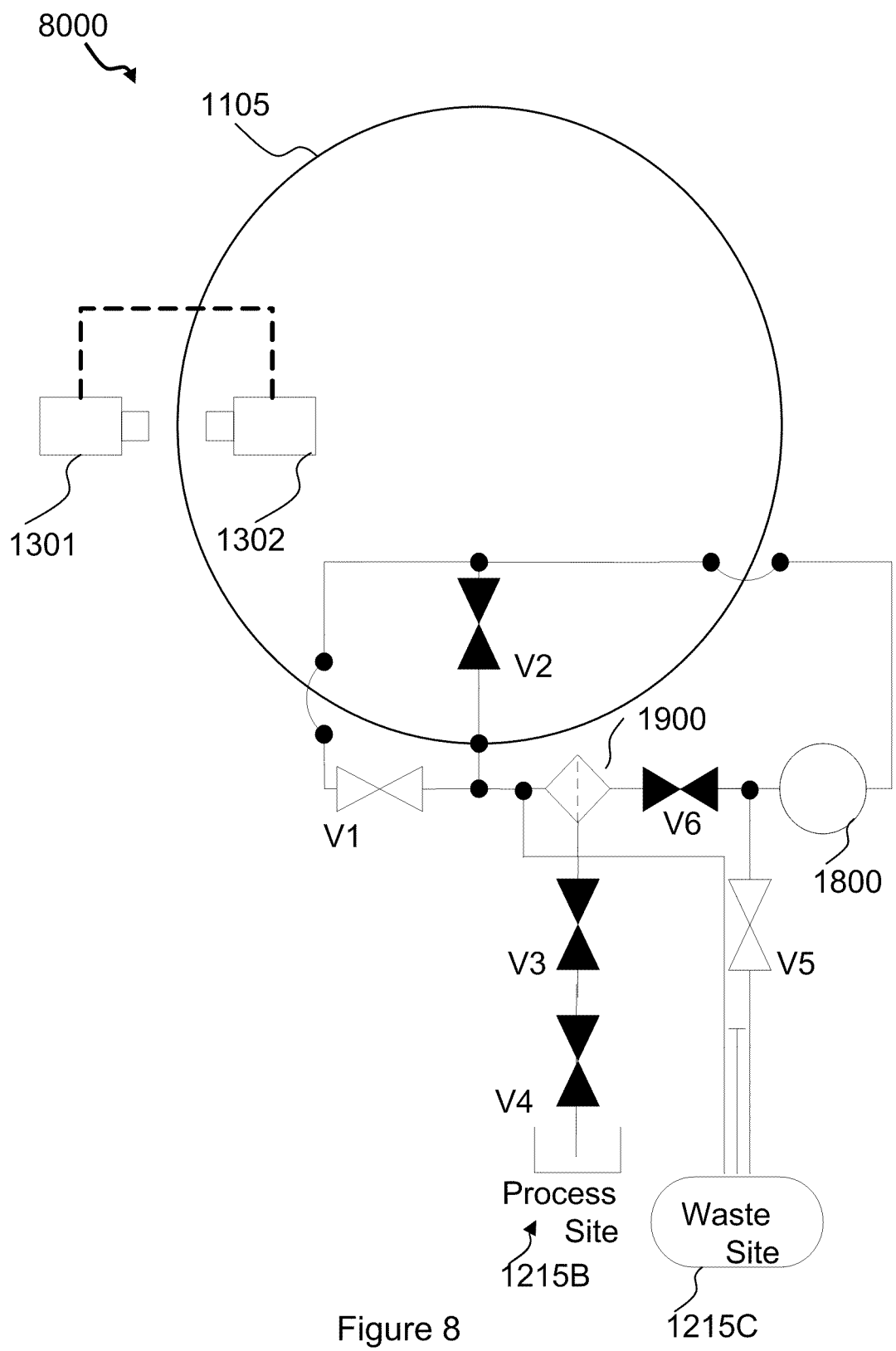
FIG. 8 is a schematic illustration of a piping system of the sample sorter system and device, according to an embodiment of the invention.

Reference is now made to FIG. 8. For delivery on demand to process, samples 1500 are removed from receptacle 1100 to process-site 1215B by employing a pump 1800. The sample sorter system schematically illustrated and exemplified in FIG. 8 is herein referred to as being an open sample sorter device and system 8000, since annular conduit 1105 is in this embodiment exemplified as being by default open to waste-site 1215C.

Sample sorter device and system 8000 includes a supply-valve V1 and a process-valve V2 which are communicating in parallel with a sample elutriator 1900 and with annular conduit 1105. The sample sorter system further includes two process-valves V3 and V4 which are connected in series with sample elutriator 1900. A waste-valve V5 communicates in parallel with a piping that connects between pump 1800 and sample elutriator 1900. Sample elutriator 1900 is upstream of pump 1800, and optionally upstream of process-valve V3 and waste-valve V5. Waste-site 1215C communicates with both waste-valve V5 and also communicates in parallel with the piping connecting elutriator 1900 with process-valve V3.

The pair of process-valves V3 and V4 may act as a sluice to uncouple between the different pressure levels that may be respectively present between annular conduit 1105 and the waste- and process-site. Sample elutriator 1900 is installed preventing samples 1500 from being destroyed by pump 1800. After sample elutriator 1900 the transport of samples may only rely on gravitational forces. A possible scheme is shown in FIG. 8, wherein supply-valve V1 and waste-valve V5 are normally open to allow a continuous flow generated by pump 1800 for providing samples 1500 to waste. In the event a sample 1500 is detected by cameras 1301 and 1302, process-valve V2 is opened for a few microseconds (e.g., 200 ms)

to remove respective sample 1500 from annular conduit 1105. Supply-valve V1 may be closed in at least approximate synchronization with the opening of process-valve V2. For delivery on demand to process (e.g., microinjection) V6 is opened and V5 is closed until the sample passed the cell elutriator. Subsequently, process-valve V3 is first opened and closed, and in succession valve V4 is opened and closed. Otherwise stated, only one of process-valve V3 and V4 is open at a time to prevent liquid loss and pressure drop in annular conduit 1105. To move samples 1500 to waste, valve V5 is opened. It should be noted that other sequences for opening and closing valves may be implemented in respective embodiments of the invention. A detailed diagram when to switch valves depending on the inputs received from first camera 1301 and second camera 1302 according to an embodiment of the invention is exemplified in the Table 1 hereinbelow:

TABLE 1

| Camera 1301 | Camera 1302 | Pump 1800 | V1 | V2 | V3 & V4 | V5 | V6 |
|---|---|---|---|---|---|---|---|
| None | None | On | Open | Closed | Closed | Open | Closed |
| Not viable | Not viable | On | Open | Closed | Closed | Open | Closed |
| Not viable | Viable | On | Open | Closed | Closed | Open | Closed |
| Viable | Not viable | On | Open | Closed | Closed | Open | Closed |
| Viable | Viable | On | Closed | Open | Open | Closed | Open |

It should be noted that in some embodiments of the invention, sample sorter system 1000 may be configured and/or adapted such that the open/closed state of the valves outlined in Table 1 are true for the instances when a given sample 1500 is located at the inlet of the respective valve. Therefore, the switching of the valves might be performed in a sequential manner.

Sample elutriator 1900 may be embodied by a T-junction wherein the outlet to pump 1800 is directed upward and the outlet to process-site 1215B is directed downward. Thusly configured, a given sample 1500 is moved down to process-site 1215B due to gravity if the given sample 1500 has a higher density than the fluid.

Figure 9:
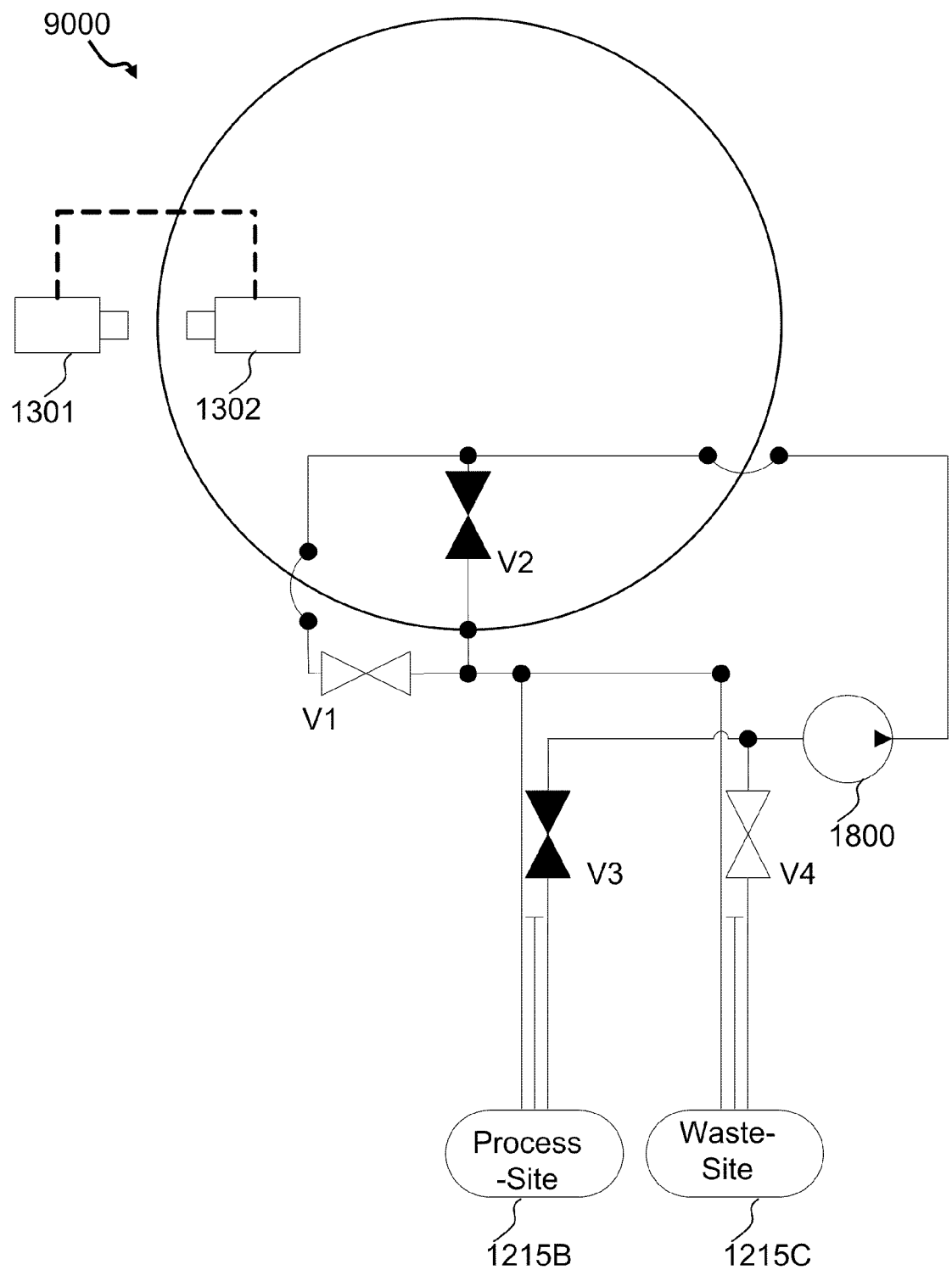
FIG. 9 is a schematic illustration of a piping system of the sample sorter system and device, according to an alternative embodiment of the invention.

Reference is now made to FIG. 9. In an embodiment wherein only viable samples 1500 have to be selected and removed from non-viable samples 1500, then a closed sample sorter device and system 9000 as schematically illustrated in FIG. 9 may be used, which can be operated at a higher speed than the open system outlined herein with respect to FIG. 8. That is, since transport of samples 1500 in closed sample sorter device and system 9000 does not rely on gravitational force. Furthermore, only four valves are needed and sample sorter device and system 9000 is operable free of sample elutriator 1900.

The possible scheme is shown in FIG. 9 and the procedure for regulating valves and pump is summarised in Table 2 hereinbelow:

TABLE 2

| Camera 1301-signal | Camera 1302-signal | Pump 1800 | V1 | V2 | V3 | V4 |
|---|---|---|---|---|---|---|
| None | None | On | Open | Closed | Closed | Open |
| Not viable | Not viable | On | Open | Closed | Closed | Open |
| Not viable | Viable | On | Open | Closed | Closed | Open |
| Viable | Not viable | On | Open | Closed | Closed | Open |
| Viable | Viable | On | Closed | Open | Open | Closed |

In analogy to what is outlined with respect to Table 1, sample sorter system 1000 may in some embodiments of the invention be configured and/or adapted such that the open/closed state of the valves outlined in Table 1 are true for the instances when a given sample 1500 is located at the inlet of the respective valve. Therefore, the switching of the valves might be performed in a sequential manner.

Figure 10:
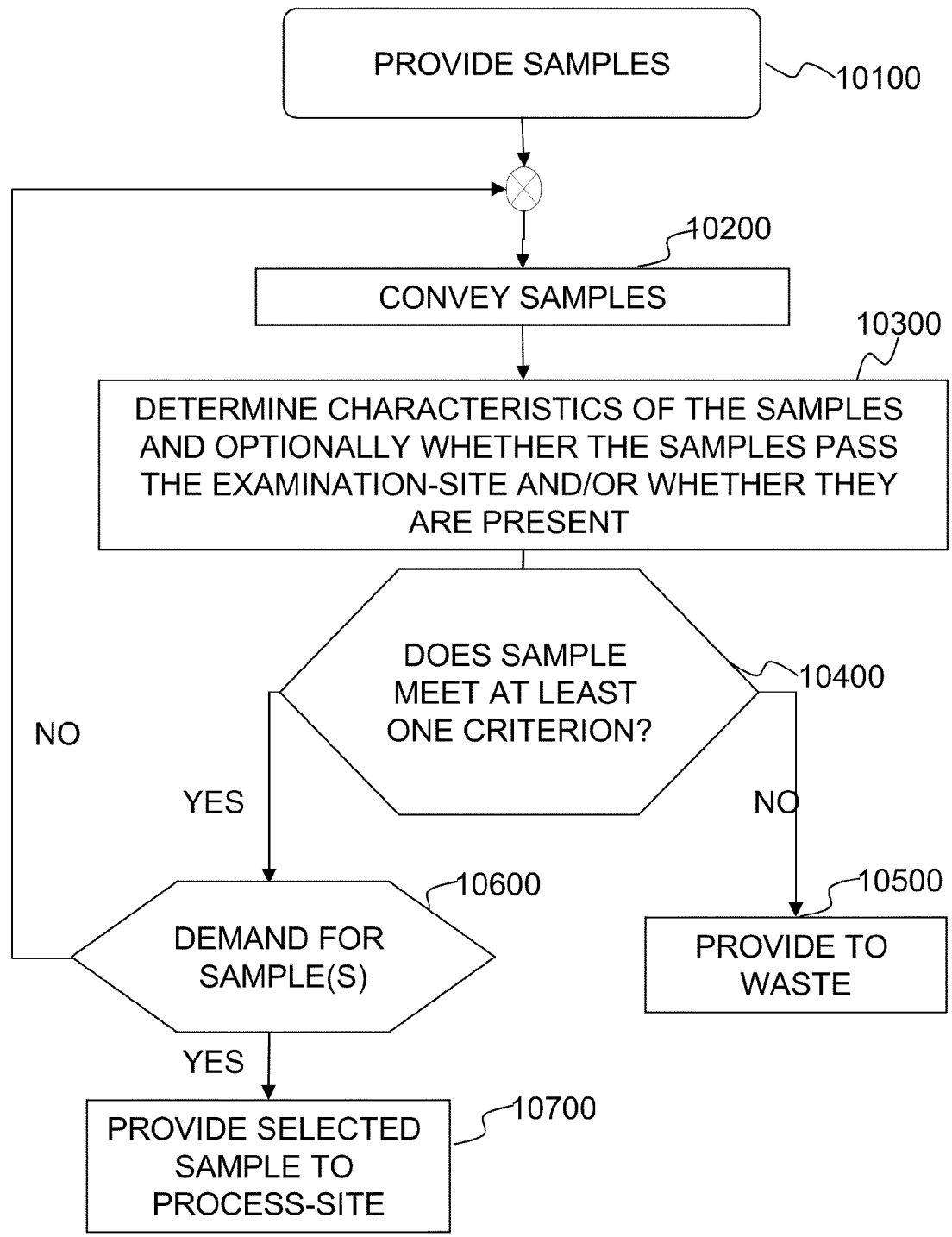
FIG. 10 is a flow-chart illustration of a method for sorting samples, according to an embodiment of the invention.

Further reference is now made to FIG. 10. In embodiments of the invention, a method for storing and sorting samples 1500 includes as is outlined by box 10100, for example, the procedure of providing a sample (e.g., cell) suspension to, e.g., receptacle 1100.

As indicated by box 10200, the method may further include the procedure of conveying samples 1500 by rotating at least on rotatable component of receptacle 1100.

As indicated by box 10300, the method may include the procedure of determining whether characteristics of samples 1500 meet the at least one criterion and optionally whether samples 1500 are present and/or pass examination-site 1310.

Generally, the method may then further include, for example, making a selection of samples 1500 according to the determined characteristics; and providing selected samples 1500 according to the determined characteristics to either one of the following: process-site 1215B, waste-site 1215C or retaining samples 1500 in circular receptacle 1100.

More specifically, as indicated by box 10400, the method may include the procedure of determining whether the determined characteristics meet the at least one predetermined criterion and if not, providing the corresponding samples 1500 to waste-site 1215C.

Conversely, if sample 1500 passing examination-site 1310 does meet the at least one predetermined quality criterion, then the method may include, as indicated by box 10600 the procedure of selecting the respective sample 1500 and determining whether there is a demand for samples 1500 meeting the at least one predetermined quality criterion. If yes, then the method may include, as indicated by box 10700, the procedure of selectively providing selected samples 1500 to process-site 1215B. If there is no demand for samples 1500 meeting the at least one criterion, then the method may include, as indicated by box 10200 again the procedure of continuing conveying selected samples 1500.

Figure 11:
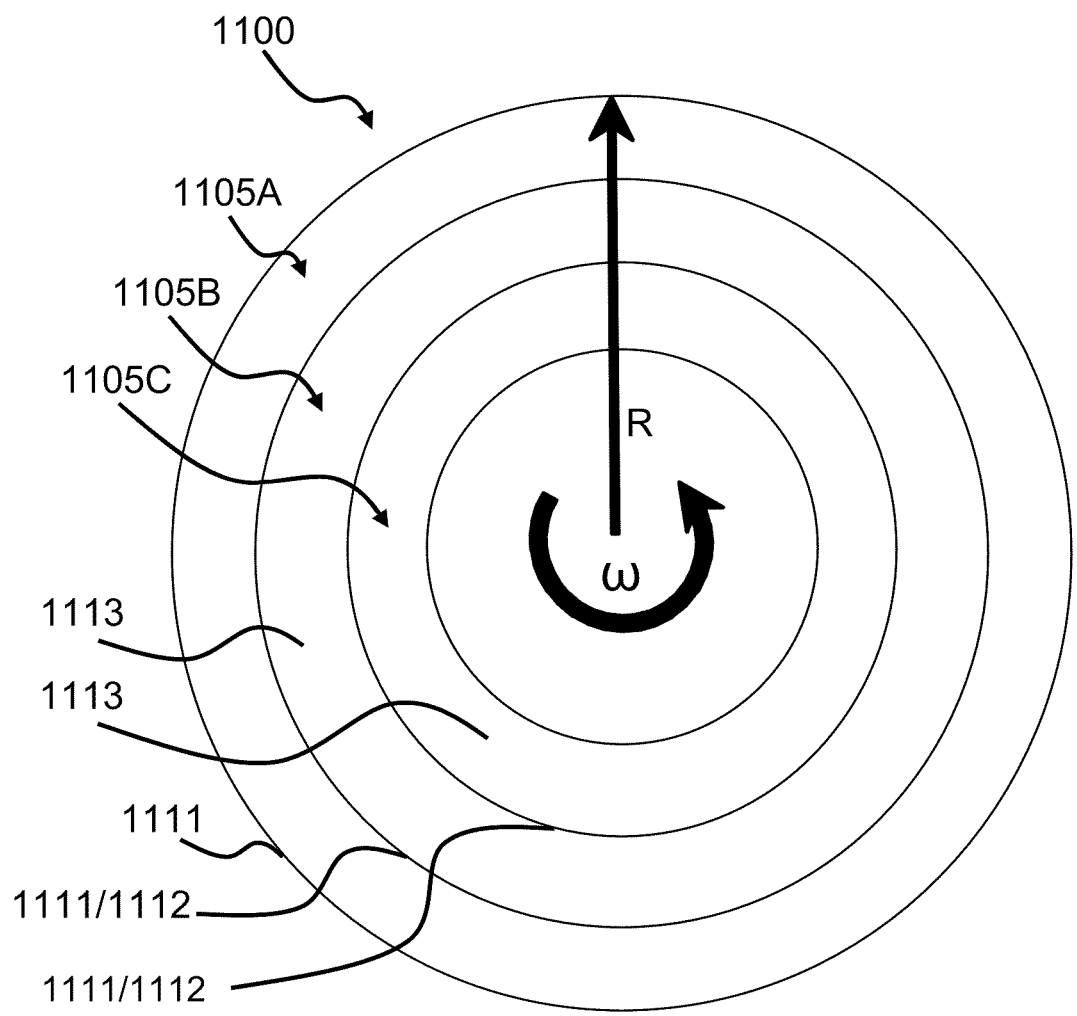
FIG. 11 is schematic top-view illustration of a receptacle, according to a yet other embodiment of the invention.

Additional reference is now made to FIG. 11. In some embodiments of the invention, receptacle 1100 may include a plurality of annular conduits such as for example annular conduit 1105A, 1105B and 1105C. In an embodiment of the invention the plurality of angular conduits may be operatively coupled with drive 1400 such that they are all rotated at the same angular velocity ω. However, this implies that the tangential velocity increases for an increase in the radius R. Alternatively, the RPM for each annular conduit 1105A, 1105B and 1105C may be set individually.

Receptacle 1100 may be made of any suitable material such as, for example, plastic (e.g., polycarbonate (PC), polymethylmethacrylate (PMMA) or polyethyleneterephtalate (PET)); and/or glass. In some embodiments of the invention, the material may be substantially transparent such to facilitate the imaging of samples 1500 through receptacle 1100 by, e.g., first camera 1301 and second camera 1302 or any other suitable imaging system.

It should be noted that although entities and/or features such as, for example, sensor 1300 according to embodiments of the disclosed invention, may be indicated hereinafter as being located in a single geographical and/or architectural location, these entities and/or features may be dispersed and/or parsed over a plurality of geographical and/or architectural locations of sample sorter device and system 1000. Accordingly, a processor (not shown) running a set of instructions (not shown) resulting in an application (not shown) which is adapted to determine for example the characteristics of samples 1500 passing examination-site 1310, may also be dispersed and/or parsed over a plurality of geographical and/or architectural locations of sample sorter device and system 1000.

In embodiments of the invention, samples sorting device and system 1000 includes a sample return feed line (via V2), wherein said return feed line feeds extracted samples back to circular receptacle 1100.

The terms "front surface", "rear surface" "right", "left", "bottom", "below", "lowered", "low", "top", "above", "elevated" and "high" as well as grammatical variations thereof as used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "front", "rear", "bottom", "below", "top" and "above" may be used herein for exemplary purposes only, to illustrate the relative positioning or placement of certain components, to indicate a first and a second component or to do both.

It should be understood that embodiments of the disclosed technique may be implemented, for example, using a machine-readable medium or article (embodied, e.g., by sensor 1300) which may store an instruction or a set of instructions that, if executed by a machine, causes the machine to perform the method in accordance with embodiments of the disclosed technique. Such a machine-readable medium may include, for example, any suitable processing platform, computing platform, computing device, processing device, computing system, processing system, computer, processor, or the like, and may be implemented by hardware and/or software, and/or firmware and/or hybrid modules.

Additionally or alternatively, embodiments of the disclosed technique such as, for example, sensor 1300, include a computer program adapted to execute the image deblurring and denoising method.

Additionally or alternatively, embodiments of the disclosed technique include a computer program comprising software code adapted to execute the image deblurring and denoising method.

It will be appreciated by persons skilled in the art that the disclosed invention is not limited to what has been particularly shown and described hereinabove.

What is claimed is:

1. A sample sorter device for receiving and sorting individual samples, the sample sorter device comprising:
   a closed-loop, annular conduit for receiving samples suspended in fluid; the closed-loop, annular conduit forming a correspondingly closed loop, annular transporting route for the fluid and the samples;
   wherein at least a portion of the closed-loop, annular conduit is a rotatable component that, when rotated, generates in the conduit a flow regime of the fluid along the annular transporting route and subjects the samples suspended in the fluid to propelling drag forces.

2. The sample sorter device according to claim 1, wherein the rotatable component is dissociated from direct frictional contact with the samples such that during rotation of the rotatable component the samples are subjected to propelling drag forces that correspond to the fluid flow around the samples.

3. The sample sorter device according to claim 1, wherein the rotatable component is selected from the group consisting of: an annular side wall; an annular cover; and an annular ground.

4. The sample sorter device according to claim 1, further comprising a cover covering the closed-loop annular conduit, the cover having side walls overlapping side walls of the closed-loop annular conduit to form a space between the cover and the side walls of the closed-loop annular conduit, the space enabling outflow of fluid from the closed-loop annular conduit over an upper edge of the side walls of the closed-loop annular conduit.

5. The sample sorter device according to claim 1, wherein the rotatable component comprises drag-increasers to increase drag between fluid received by the closed-loop annular conduit and the rotatable component.

6. The sample sorter device according to claim 1, wherein the flow regime in the annular conduit is laminar.

7. The sample sorter device according to claim 1, further comprising a second rotatable component which can be rotated by the drive or can remain static during operation of the device.

8. A sample sorter system for receiving and sorting individual samples, the sample sorter system comprising:
   a drive;
   a power source;
   a closed-loop annular conduit for receiving fluid and the samples to be sorted; the closed-loop annular conduit defining a transporting route for the fluid and the samples to be sorted, when fluid is distributed throughout the closed-loop annular conduit, the samples are suspended therein; the closed-loop annular conduit including an upper part and a lower part wherein at least one portion of at least one of the upper and lower parts is a rotatable component operatively coupled to the drive and to the power source such that actuation of the drive rotates the rotatable component, the rotatable component configured to subject samples suspended in the fluid to propelling drag forces when rotated, wherein rotation of the rotatable component generates a fluid flow around the samples propelling the samples and fluid along the transporting route; and
   at least one piping system operatively coupled to the closed-loop annular conduit; the piping system including:
   i) a sample-removal piping system operative to selectively remove samples from the closed loop annular conduit during rotation, the sample-removal piping system including at least one of a release valve, a suction pump, and a sample elutriator;
   ii) a supply valve and a process valve communicating in parallel with the sample elutriator and with the closed-loop annular conduit;
   iii) a first process valve and a second process valve connected in series with the sample elutriator; and
   iv) a waste valve communicating in parallel with a piping that connects between the suction pump and the sample elutriator when the sample elutriator is upstream of the suction pump.

9. The sample sorter system according to claim 8, further comprising a second rotatable component which can be rotated by the drive or can remain static during operation of the system.

10. The sample sorter system according to claim 8, further comprising at least a second closed-loop annular conduit such that the system includes a plurality of closed-loop annular conduits.

11. The sample sorter system according to claim 8, wherein the walls of the closed-loop annular conduit are adjustable to successively align the samples in the closed-loop annular conduit.

12. The sample sorter system according to claim 8, wherein walls of the closed-loop annular conduit are adjustable to accommodate samples having diameters in a range from about 20 to 2000 microns.

13. The sample sorter system according to claim 8, wherein the at least one piping system further comprises a supply-piping, a process-piping, a waste-piping, and a sample-return feed line, wherein the sample-return feed line is operative to return samples removed the closed-loop conduit back to the closed-loop annular conduit.

14. A method for sorting samples comprising the following procedures: providing samples to the annular conduit of the sample sorter device according to claim 1; conveying the samples by rotating the rotatable component of the annular conduit and determining characteristics of the samples.

15. The method of claim 14, further comprising the procedures of: selecting samples according to the determined characteristics; and providing the samples selected according to the determined characteristics to a process-site or, a waste-site, or retaining said samples in the annular conduit.

16. The sample sorter system according to claim 8, further comprising a sensor for operatively determining whether a sample is present in the closed-loop annular conduit and for operatively determining at least one characteristic of a sample present in the closed-loop annular conduit.

17. The sample sorter system according to claim 16, wherein the sensor is implemented by at least one selected from the group consisting of at least one camera, at least one capacitance-based sensor, at least one light barrier, and at least one fluorescence-based sensor.

18. The sample sorter system according to claim 17, wherein the sensor is implemented by two cameras positioned for two-sided imaging of samples in the closed-loop annular conduit.

19. The sample sorter system according to claim 17, wherein the sensor is responsively coupled with the sample-removal piping such that any sample that activates the sensor can be removed from the closed-loop annular conduit by the sample-removing piping.

20. The sample sorter system according to claim 16, wherein the closed-loop annular conduit is made of a substantially transparent material to facilitate imaging of the samples.

* * * * *